US007842460B2

(12) United States Patent
Butt et al.

(10) Patent No.: US 7,842,460 B2
(45) Date of Patent: Nov. 30, 2010

(54) METHOD FOR ASSESSING PROTEOLYTIC ENZYME ACTIVITY USING UBIQUITIN FUSION SUBSTRATE

(75) Inventors: Tauseef R. Butt, Malvern, PA (US); Alejandro Bernal, Malvern, PA (US)

(73) Assignee: Progenra Inc., Malvern, PA (US)

( * ) Notice: Subject to any disclaimer, the term of this patent is extended or adjusted under 35 U.S.C. 154(b) by 0 days.

(21) Appl. No.: 11/156,707

(22) Filed: Jun. 21, 2005

(65) Prior Publication Data

US 2006/0040335 A1    Feb. 23, 2006

Related U.S. Application Data

(60) Provisional application No. 60/580,900, filed on Jun. 21, 2004.

(51) Int. Cl.
| | |
|---|---|
| C12Q 1/37 | (2006.01) |
| C12N 9/48 | (2006.01) |
| G01N 33/53 | (2006.01) |
| G01N 33/537 | (2006.01) |

(52) U.S. Cl. .................... 435/6; 435/7.1; 435/7.92; 435/23; 435/24; 435/212

(58) Field of Classification Search ........................ None
See application file for complete search history.

(56) References Cited

U.S. PATENT DOCUMENTS

| 5,503,977 | A | 4/1996 | Johnsson | |
|---|---|---|---|---|
| 6,392,028 | B1 * | 5/2002 | Rice et al. | 536/23.72 |
| 2004/0053324 | A1 * | 3/2004 | Wong et al. | 435/7.1 |
| 2005/0084864 | A1 * | 4/2005 | Rossner et al. | 435/6 |

FOREIGN PATENT DOCUMENTS

| WO | 02/27020 | 4/2002 |
|---|---|---|
| WO | 2004/092211 | 10/2004 |

OTHER PUBLICATIONS

Lee et al, "A Method for Assaying Deubiquitinating Enzymes," (Biol. Proc. Online) 1998, vol. 1, No. 1, pp. 92-99.*

Ciechanover et a, "The Ubiquitin-mediated Proteolytic Pathway: Mode of Action and Clinical Implications," (Journal of Cellular Biochemistry), 2000, Supplement, 34, pp. 40-51.*
Vu et al, "Ubiquitin-Mediated Proteolysis and Human Disease," (Molecular Genetics and Metabolism), 2000, vol. 71, pp. 261-266.*
Gehring et al. (1995) J. Biol. Chem. 270(38): 22507-513.*
Nicholson et al. (2008) Characterization of ubiquitin and ubiquitin-like-protein isopeptidase activities. Prot. Sci. 17: 1035-1043.*
Arnold et al. (2006) Small ubiquitin-like modifying protein isopeptidase assay based on poliovirus RNA polymerase activity. Anal. Biochem. 350: 214-221.*
Leach et al. (2009) Detection and Characterization of SUMO Protease Activity Using a Sensitive Enzyme-Based Reporter Assay. In Ulrich, H.D. (ed.) Meth. Mol. Biol.: SUMO Protocols, Humana Press, New York., vol. 497, Chapter 18, pp. 269-281.*
Dantuma, N.P., et al., "Short-Lived Green Fluorescent Proteins for Quantifying Ubiquitin/Proteasome-Dependent Proteolysis in Living Cells," Nature Biotechnology (2000) 18:538-543.
Gohara, D.W., et al., "Production of "Authentic" Poliovirus RNA-Depenent RNA Polymerase (3Dpol) by Ubiquitin-Protease-Mediated Cleavage in Escherichia Coli," Protein Expression and Purification (1999) 17:128-138.
Malakhov et al., "SUMO Fusions and SUMO-specific Protease for Efficient Expression and Purification of Proteins," Journal of Structural and Functional Genomics (Mar. 2004) 5:75-86.

* cited by examiner

*Primary Examiner*—Lisa J Hobbs
(74) *Attorney, Agent, or Firm*—Dann, Dorfman, Herrell & Skillman; Robert C. Netter, Jr.

(57) ABSTRACT

Methods and kits for assessing proteolytic enzyme activity and a modulator's effect thereof employ a Ubiquitin or Ubiquitin-like Protein and a signal producing structure. The corresponding fusion polynucleotide is employed for production of transgenic cells, plants and animals that may be produced by stably transfection, optionally transforming the cell, plant or animal with a Ubiquitin-, UBL- or their C-terminal binding functional fragment-Reporter fusion polynucleotide. A method of diagnosing a disease or condition, comprises contacting or administering a sample obtained from a subject suspected of being afflicted with the disease or condition with the cell, plant or animal, detecting any signal produced by the reporter in the presence of the sample and comparing the signal to controls for 0% and 100% signals.

25 Claims, No Drawings

SEQUENCE LISTING

```
<160> NUMBER OF SEQ ID NOS: 6

<210> SEQ ID NO 1
<211> LENGTH: 34
<212> TYPE: DNA
<213> ORGANISM: Artificial Sequence
<220> FEATURE:
<223> OTHER INFORMATION: Synthetic Primer

<400> SEQUENCE: 1
gcaggtctca aggtggtgaa atccagtgga tgag                                   34

<210> SEQ ID NO 2
<211> LENGTH: 24
<212> TYPE: DNA
<213> ORGANISM: Artificial Sequence
<220> FEATURE:
<223> OTHER INFORMATION: Synthetic Primer

<400> SEQUENCE: 2
gcaggatccc tagtggtggt ggtg                                              24

<210> SEQ ID NO 3
<211> LENGTH: 35
<212> TYPE: DNA
<213> ORGANISM: Artificial Sequence
<220> FEATURE:
<223> OTHER INFORMATION: Synthetic Primer

<400> SEQUENCE: 3
gtcaggtctc aaggttgcgg tattgtcggt atcgc                                  35

<210> SEQ ID NO 4
<211> LENGTH: 30
<212> TYPE: DNA
<213> ORGANISM: Artificial Sequence
<220> FEATURE:
<223> OTHER INFORMATION: Synthetic Primer
```

```
-continued

<400> SEQUENCE: 4
gtcaggatcc tcatccttcg ttatgcattt                                         30

<210> SEQ ID NO 5
<211> LENGTH: 36
<212> TYPE: DNA
<213> ORGANISM: Artificial Sequence
<220> FEATURE:
<223> OTHER INFORMATION: Synthetic Primer

<400> SEQUENCE: 5
gatcggtctc aaggtggact cctggagctg gcaggg                                  36

<210> SEQ ID NO 6
<211> LENGTH: 31
<212> TYPE: DNA
<213> ORGANISM: Artificial Sequence
<220> FEATURE:
<223> OTHER INFORMATION: Synthetic Primer

<400> SEQUENCE: 6
gatcggatcc tcaattgcac ttgggagagt c                                       31
```

METHOD FOR ASSESSING PROTEOLYTIC ENZYME ACTIVITY USING UBIQUITIN FUSION SUBSTRATE

RELATED APPLICATIONS

This patent claims priority of the filing date of Jun. 21, 2004 of U.S. Provisional Application 60/580,900, entitled "Methods for Assessing Isopeptidase Activity.

BACKGROUND OF THE INVENTION

1. Field of Invention

This patent provides materials and methods for the qualitative and quantitative assessment of ubiquitin and ubiquitin-like proteolytic enzyme activity as well as the discovery of novel enzymes, for evaluating and/or screening compounds for their effects on proteolytic enzyme activity, and for detecting activity in biological samples, which is useful for the diagnosis of conditions and diseases associated with altered enzyme levels, amounts, sequences and/or activities. This technology is also incorporated into disease models in the form of transgenic cells, plants and animals.

2. Background of the Invention

Ubiquitin (Ub) isopeptidases were first cloned over a decade ago. Up to this point, however, there existed no suitable assay for proteolytic enzymes specific for Ub or Ubiquitin-like Proteins (UBL) or for rapid screening of modulators or inhibitors of the enzyme. Most of the assays that are currently in use rely on cleavage of linear Ub-fusions, which are either produced in $E.\ coli$, e.g. tetra-Ub, Ub-CEP52, Ub-GSTP1, Ub-DHFR, Ub-PESTc, and the like, or synthesized chemically. In these assays the reaction products are either analyzed by gel electrophoresis, or selectively precipitated and then analyzed by liquid scintillation spectrometry.

These assays have significant drawbacks, e.g. that gel-based approaches are labor intensive and expensive. Although selective precipitation/scintillation count provides quantitative results and allows the processing of larger numbers of samples than gel-based assays, it requires centrifugation, and supernatant separation. Ubiquitin-7-amido-4-methylcoumarin (Ub-AMC) is a fluorogenic substrate for High Throughput Screening (HTS) that is commercially available and easy to use. However, unlike Ubiquitin C-terminal Hydrolases (UCHs), most Ubiquitin Specific Proteases (USPs) do not cleave small groups from the Ubiquitin (Ub) molecule. AMC, in addition, is highly hydrophobic and, based on its own interactions with test compounds, may give rise to false positives in screenings. Other ways to detect cleavage, e.g. High Pressure Liquid Chromatography (HPLC) and mass-spectroscopy have also been used although they have their own drawbacks. Furthermore, none of the prior art methods are suitable or adaptable to high throughput screening, which requires simple (minimal number of steps) assays that may be conducted using multi-well plates, and whose endpoints are read directly from the plates.

There is, therefore, a need for assays and kits that are simple and relatively inexpensive in nature while at the same time being suitable for conducting high throughput screening for modulators of ubiquitin or Ubiquitin-like Protein (UBL) proteolytic enzymes.

SUMMARY OF THE INVENTION

One aspect of the present invention relates to a method for assessing proteolytic enzyme activity, which method comprises providing a fusion polymer comprising a first polymer that comprises Ubiquitin or a Ubiquitin-like protein (UBL) or a functional C-terminal segment thereof and a second polymer comprising a free N-terminal amino acid required for detection; wherein the first and second polymers are operatively linked to one another through the UBL C-terminus and the second polymer N-terminus;

contacting the fusion polymer with a proteolytic enzyme that cleaves at the UBL C-terminus;

detecting a signal associated with either amount or activity of cleaved polymer; and establishing a correlation between the cleaved polymer's signal to the proteolytic enzyme's activity.

For the practice of the above method this patent provides a kit for assessing proteolytic enzyme activity, comprising a fusion polymer comprising a first polymer that comprises Ubiquitin or a ubiquitin-like protein (UBL) or a C-terminal segment thereof and a second polymer comprising a polypeptide requiring a free N-amino acid terminus for detection; wherein the first and second polymers are operatively linked to one another through the Ubiquitin or UBL C-terminus and the second polymer N-terminus; and instruction for conducting the proteolytic enzyme assay, detecting a signal associated with the amount or activity of the first and/or second polymers, and establishing a correlation of the detected signal to the enzyme's proteolytic activity; and optionally a source of a proteolytic enzyme that cleaves at the UBL C-terminus and several other components.

Another aspect of the invention relates to a method for screening compounds for their effect on proteolytic activity, comprising obtaining a fusion polymer comprising a first polymer that comprises Ubiquitin or a ubiquitin-like protein (UBL) or a binding functional C-terminal segment thereof and a second polymer comprising a free N-terminus amino acid; wherein the first and second polymers are operatively linked to one another through the N-C-termini;

contacting the fusion polymer with a UBL C-terminus cleaving proteolytic enzyme under conditions effective for cleavage to occur;

detecting a signal associated with an amount of cleavage to obtain a 100% cleavage signal;

repeating the contacting and detecting steps in the presence of a full inhibitor of proteolytic enzyme activity to obtain a 0% cleavage signal;

obtaining a set of compounds;

separately repeating the fusion polymer obtaining, contacting and detecting steps in the presence of each compound to obtain a cleavage signal;

normalizing each compound cleavage signal by reference to the 0% and 100% cleavage signal and assigning a proteolytic enzyme activity value to each compound.

For the practice of this second method this patent provides a proteolytic enzyme activity modulator screening kit, comprising a fusion polymer comprising a first polymer that comprises Ubiquitin or a ubiquitin-like protein (UBL) or a C-terminal segment thereof and a second polymer comprising a polypeptide requiring a free N-amino acid terminus for detection; wherein the first and second polymers are operatively linked to one another through the Ubiquitin or UBL C-terminus and the SECOND polymer N-terminus; and instruction for conducting the proteolytic enzyme assay, detecting a signal associated with the amount or activity of the first and/or second polymers, and establishing a correlation of the detected signal to the enzyme's proteolytic activity for a plurality of modulators and controls; and optionally a source of a proteolytic enzyme that cleaves at the Ubiquitin or UBL C-terminus, and other components suitable for different embodiments.

This invention also relates to a transgenic cell, plant or animal, comprising an Ubiquitin- or UBL-reporter fusion polynucleotide that is optionally integrated into the cell, plant or animal's chromosome; wherein the Ubiquitin or UBL-specific isopeptidase is associated with a specific disease or condition or a family thereof.

The transgenic cell, plant or animal may be produced by
  obtaining a cell, plant or animal;
  obtaining an Ubiquitin-, UBL- or their C-terminal binding functional fragment-Reporter fusion polynucleotide;
  obtaining a hybrid vector carrying the hybrid polynucleotide operatively linked to a vector; and
  stably transfecting the hybrid vector into the cell, plant or animal.

Also described in this patent is a method of diagnosing a disease or condition, comprising
  obtaining the cell, plant or animal of the invention, or fractions or tissue thereof, wherein the Ubiquitin or UBL-specific isopeptidase is associated with a disease or condition;
  contacting or administering a sample obtained from a subject suspected of being afflicted with the disease or condition with the cell, plant or animal;
  detecting any signal produced by the reporter in the presence of the sample; and comparing the signal to controls for 0% and 100% signals.

Other objects, advantages and features of the present invention will become apparent to those skilled in the art from the following discussion.

DETAILED DESCRIPTION OF THE PREFERRED EMBODIMENTS OF THE INVENTION

This invention arose from a desire by the inventors to improve on prior art methods of assaying proteolytic enzyme activity associated with Ubiquitin and Ubiquitin-like Proteins (UBL). Upon observation of the drawbacks inherent in existing methods, the inventors researched the field for an opportunity to provide a method that is simple, has easily determinable end-points, and is suitable or adaptable to high throughput screening, automation and computerization of data collection. The present enzyme activity assays and kit employ relatively inexpensive elements, require a small number of operations, may be conducted using multi-well plates and therefore automated, and their endpoints may be directly read therefrom and data collection and analysis computerized. These are also characteristics of the present method and kit for high throughput screening of modulators of Ubiquitin or Ubiquitin-like Protein (collectively UBL) proteolytic enzymes. The present technology answers research and health care industry needs by providing rapid, inexpensive, selective and simple methods for assaying the activity of UBL enzymes, which are adaptable to high-throughput screening for UBL proteolytic enzyme modulators, and useful for diagnosing diseases and conditions that are associated with UBLs proteolytic enzymes, such as isopeptidases and the like, and for screening for new enzymes and UBL enzyme modulators.

The present invention relates to the field of enzymatic activity, its modulation and detection, and more specifically to the activity of Ubiquitin and Ubiquitin-like Protein (LUBL) proteolytic, e.g. isopeptidase/hydrolase/protease, enzymes, their modulation and detection. The patent provides kits and methods for qualitative and/or quantitative assessment of UBL proteolytic enzyme activity, a method for evaluating or screening compounds and agents for their effects on enzyme activity, and a method for detecting the activity in biological samples. The ubiquitin-proteasomal pathway has been validated by the introduction and clinical success of Velcade® in the treatment of refractory relapsed multiple myeloma. See, Adams (2002).

This pathway is purported to regulate cell content and/or compartmentalization of most proteins, and is a promising, though under-exploited arena for drug discovery. See, Ciechanover (2001); Ciechanover (2003). At any given time the cellular content of a protein is believed to be regulated by a combination of its synthetic and degradation rates, with each protein having a characteristic pattern of synthesis and degradation to ensure proper cellular function. Degradation is believed to occur in different ways. Extracellular or membrane-associated proteins are believed to be generally degraded in lysosomes, to which they are directed by Golgi-endosomal apparati. Soluble, cytoplasmic proteins are believed to be degraded in a regulated fashion via the ubiquitin-proteasomal pathway. The latter pathway is thought to account for the degradation of up to about 90% of all abnormal, misfolded proteins and most short-lived, regulatory proteins in a cell. In addition, proteasomes are also believed to be involved in the breakdown of most longer-lived proteins. It is estimated that the ubiquitin-proteasome pathway may account for 80-90% of cellular protein degradation. See, Lee and Goldberg (1998). Targets of the ubiquitin-proteasome pathway comprise cell cycle and division regulators, ion channels, tumor suppressors and transcription factors, among many others. See, Hershko and Ciechanover (1998); Vu and Sakamoto (2000); Conaway, et al. (2002). Because this represents a broad range of substrates, it is taken as an implication of the involvement of the Ub-proteasome pathway in cell cycle progression, apoptosis, immune response, development, transcriptional regulation, signal transduction, and receptor down-regulation, among other functions. Because the pathway occupies such a central role in cellular processes, the pathogenesis associated with various diseases, e.g. Parkinson's disease, cervical cancer, and von Hippel Lindau syndrome, among others, have been linked to aberrations this pathway. See, for example, Kitada, et al. (1998); Leroy, et al. (1998); Kato (1999); Swinney (2001).

Ubiquitin is a 76 amino acid protein that appears to be the most conserved eukaryotic structure. It has not been found to be encoded as a monomer but, rather, to be expressed as a C-terminal extension protein. For example, two of the mammalian ribosomal proteins are encoded as ubiquitin fusion proteins. It is believed that all eukaryotic cells contain potent ubiquitin C-terminal hydrolases, all of which cleave these fusion proteins at the Ubiquitin carboxy (C-) terminus. In addition, it has been shown that artificial fusions of the ubiquitin gene product may be expressed and cleaved in eukaryotic cells. It has been shown that prokaryotes, e.g. *E. coli*, neither contain ubiquitin nor the ubiquitin pathway. A number of proteins homologous to ubiquitin are known, e.g. SUMO, Nedd8, ISG15, Apg8, Apg12, FAT10, Urm1, Hub, GDX, HCG-1, BMSC-UBP, and UBi, among others. The homology of these Ubiquitin-like proteins (UBL) proteins to ubiquitin is generally limited to about 15 to 30% of their amino acid sequence, and many of them are encoded as precursor proteins and/or to contain C-terminal extensions. These "fusions" produced by eukaryotic cells are immediately processed by highly specific hydrolases, suggesting that UBL hydrolases (proteases) play an important role in controlling the level of mature UBLs. The C-terminus of ubiquitin is covalently conjugated to N-amino groups of target proteins by a variety of enzymes. Following the ligation of a single molecule to its target protein, a chain of ubiquitin molecules may be generated and extended by covalent conjugation of C-termini of ubiquitin to one of its 6 lysine N-amino groups to form poly-ubiquitin chains. Polyubiquitination is believed to act as a signal for proteolysis, and the ubiquitinated proteins are thought to be recognized by the proteasome and degraded, and the ubiquitin molecule recycled. Many UBLs are covalently conjugated to target proteins via isopeptide bonds in a manner similar to Ubiquitin. Although their actual functions are not completely understood, UBLs appear to be conjugated to their target proteins, and de-conjugated from them, in a highly regulated fashion that involves elaborate pathways that are known in the art. See, for example, Glickman and Ciechanover (2002).

It is estimated that in excess of 65 isopeptidase genes exist in the human genome. Isopeptidases are believed to play an important role in regulating the fate of UBLUBL-modified proteins. For example, ubiquitin may be de-conjugated by an isopeptidase. When this occurs, the target protein may no longer be channeled to and recognized by the proteasome for degradation and, therefore, will remain undegraded in the cell. Isopeptidases, therefore, are thought to play an important role in editing ubiquitin function and in cellular pathologies that may develop as a consequence thereof. In addition to acting as a signal for proteolysis, the mono-ubiquitination of proteins is believed to be involved in the control of various cellular activities, e.g. endocytosis, chromatin remodeling, signal transduction, and many others. Although the precise role of many UBL conjugations and de-conjugations remains to be mapped individual UBL proteolytic enzymes, e.g. isopeptidases and hydrolases, are clearly involved in the process.

This invention will be described generally, as well as specifically by means of examples with specific fusion polymers, e.g. proteins, Ubiquitin, Ubiquitin-like proteins (UBLs), both collectively referred to as UBLs, and are all proteolytic enzymes across the phylogeny that recognize and cleave the UBL C-terminus in a fusion protein. These UBL may be bound to reporter or signaling molecules such as all reporter proteins, all binding pairs, and the like, described below by means of examples to form inactive fusion polymers. This patent broadly encompasses all members of a genus, all members of a species, and the like, of the fusion members and the proteolytic enzymes as long as these members belong to the functional category assigned and described to a molecule. The covalent conjugation of a UBL, e.g. SUMO, to a Ran-gap protein, for example, is believed to control the protein's translocation between the nucleus and the cytosol. This type of mechanism may be exploited for therapeutic purposes. For example, the SUMOylation of a dormant cytosolic transcription factor translocates active protein to the nucleus, where it may act to turn on a tumor suppressor gene. The inhibition of a SUMO protease by an exogenous agent, e.g. a small molecule, in this case could stabilizing the SUMO fusion and, thus, display anti-cancer activity. The regulation of a SUMO protease, e.g. Ulp1, function by a small molecule could bring about a therapeutic anti-cancer benefit. Similarly, the conjugation and de-conjugation of other UBLs, e.g. ISG-15, Apg8, or Nedd8, may be controlled by their respective proteolytic enzymes, e.g. hydrolases (proteases) including UBP43/, Apg4, and NUB1-linked C terminal hydrolase/NEDP1/ UCH-L1/UCH-L3/COP9, respectively. This could lead to a regulation of the functions of their respective protein modification pathways. ISG15 is an important regulator of inflammatory responses to viral infection that is conjugated to key regulators of signal transduction. See, Malakov (2003). ISG15 is one of the most strongly induced genes after interferon (IFN) treatment, and is significantly induced by influenza B virus, lipopolysaccharide (LPS), and genotoxic stress. It is processed from a 17 kDa precursor, and conjugated to specific proteins in the conserved Ubiquitin-conjugation pathway. An ISG15-specific isopeptidase, UBP43, is also suitable for use with this invention. See, Malakhov et al (2002); Malakhova et al (2002)

Ubiquitin is cleaved from substrates by proteolytic enzymes generally referred to as ubiquitin isopeptidases, or ubiquitin hydrolases, proteases, or de-ubiquitinating enzymes ("DUBs"). Isopeptidases are a family of cysteine hydrolases (proteases) that specifically cleave ubiquitin-derived substrates of the general structure Ub-X, where X=any number of leaving groups ranging from small thiols and amines to Ub and other proteins. See, for example, Dang, et al. (1998). Proteolytic enzymes such as isopeptidases, therefore, are believed to act to reverse the modification of proteins by ubiquitin or ubiquitin-like proteins. See, Wilkinson (2000). Among proteolytic enzyme families, there are two major families of isopeptidases: Ubiquitin C-terminal hydrolases (UCH) and Ubiquitin-specific proteases (USP), both of which are thiol active site proteases. In addition, there is known a family of metalloprotease isopeptidases that contain a unique JAMM (Jab1/MPN domain) isopeptidase active site. See, Lundgren, et al. (2003); Hochstrasser (2002); Verma, et al. (2002); Yao and Cohen (2002). In addition, it is also known the existence of a family of cysteine proteases referred to as otubains that appear to be highly specific ubiquitin isopeptidases, although some appear to have no sequence homology to known ubiquitin isopeptidases. See, Balakirev, et al. (2003). Proteases specific for ubiquitin-like proteins (UBLs) are also known.

The UCH enzyme family is believed to cleave Ub primarily when present with short C-terminal extensions. However, these proteases may be associated with larger protein substrates, including Ub precursors and Ub adducts with small amines and thiols, and are believed to be involved in cellular signaling and nuclear-cytoplasmic transport. See, Layfield, et al. (1999). The USP enzyme family exhibits no homology to UCHs, and may cleave ubiquitin from a range of protein substrates. See, for example, Wilkinson (1997); D'Andrea and Pellman (1998); Wilkinson (1998); Chung and Baek (1999); Yan, et al. (2000). While USPs show significant differences in size and amino acid sequences, they share several highly homologous patches around the residues required for catalytic activity. The sequencing of the human genome uncovered 53 USP encoding genes and 4 UCH genes. Both, UCHs and USPs, are potential targets for therapeutic intervention. The processes of mono- and poly-ubiquitination are highly dynamic, and are characterized by rapid addition and/ or removal of ubiquitin from proteins. The UCH enzyme family comprises, in general, relatively small, about 20 to 30 kDa, proteins with some exceptions, e.g. UCH37, a 37 kDa proteasome-bound enzyme, and BAP1, an 81 kDa protein that binds to BRCA1. See, Jensen, et al. (1998). Their principal substrates are believed to be Ub precursors and Ub adducts with small molecules containing amine and thiol residues. Layfield, et al. (1999). Human UCHL1 and UCHL3 may hydrolyze ε-linked amide bonds at the Ub C-terminus as well as α-linked peptide bonds. See, Johnston, et al. (1997). The UCH family includes yeast YUH1, mammalian UCHL1, also known as PGP9.5, UCH-L3, UCH37, Bap1, and many others as well as the corresponding enzyme families of other species. See, for example, Day, et al. (1990); Larsen, et al. (1996). The USP family generally comprises larger, 41 kDa and above, proteins that exhibit little to no homology to UCHs, and cleave ubiquitin from a range of protein substrates. See, Wilkinson (1997); D'Andrea and Pellman (1998); Wilkinson (1998); Chung and Baek (1999); Yan, et al. (2000). Although most USPs may hydrolyze linear Ub fusions, e.g. α NH-peptide bond, their primary role is believed to be the removal of Ub molecules that are conjugated to proteins by εNH2-isopeptide linkages by lysine side chains. There are isopeptidases that are associated with Ubiquitin-like proteins as well. For example, there are several yeast and human proteases, e.g. ULP1 and Ulp2, and SENP1 and SENP2 that may remove SUMO from the ε-amino lysine groups as well as from artificial linear SUMO fusions. See, Li and Hochstrasser (1999); Li and Hochstrasser (2000); Gong, et al. (2000). Examples of human isopeptidases are shown in Table 1 below. However, other human proteolytic enzymes that recognize the C-terminus of Ubiquitin or an Ubiquitin-like protein are also suitable, as are similar enzymes from other species, either prokaryotic or eukaryotic.

TABLE 1

Examples of Human Isopeptidases

|    | Name    | Synonym                      | MW (kDa) |
|----|---------|------------------------------|----------|
| 1  | CYLD    | CYLD1, KIAA0849              | 10.7     |
| 2  | USP9X   | DFFRX, USP9, FAFX            | 28.9     |
| 3  | USP9Y   | DFFRY, USP10, FAFY           | 29.1     |
| 4  | OTUB1   | OTB1, OTU1, HSPC263          | 31.3     |
| 5  | OTUB2   | C14orf137, OTB2, OTU2        | 27.2     |
| 6  | USP10   | KIAA0190                     | 87       |
| 7  | USP11   | UHX1                         | 105      |
| 8  | USP12   | UBH1m, USP12L1               | 41.2     |
| 9  | USP13   | ISOT3                        | 97.3     |
| 10 | USP14   | TGT                          | 55.9     |
| 11 | USP15   | KIAA0529                     | 112.4    |
| 12 | USP16   | UBPM                         | 93.6     |
| 13 | USP18   | UBP43                        | 43       |
| 14 | USP19   | KIAA0891, ZMYND9             | 151.3    |
| 15 | USP20   | KIAA1003, LSFR3A             | 102      |
| 16 | USP21   | USP23, NEDD8-specific protease | 62.6   |
| 17 | USP22   | KIAA1063                     | 66.6     |
| 18 | USP24   | KIAA1057                     | 112.4    |
| 19 | USP25   | USP21                        | 125.7    |
| 20 | USP26   |                              | 104      |
| 21 | USP28   |                              | 122.5    |
| 22 | USP29   |                              | 104      |
| 23 | USP30   |                              | 58.5     |
| 24 | USP32   | USP10                        | 181.7    |
| 25 | USP33   | KIAA1097, VDU1               | 106.7    |
| 26 | USP35   | KIAA1372, USP34              | 113.4    |
| 27 | USP36   | KIAA1453                     | 122.6    |
| 28 | USP37   | KIAA1594                     | 110      |
| 29 | USP38   | KIAA1891                     | 116.5    |
| 30 | USP40   |                              | 129.6    |
| 31 | USP42   |                              | 130.6    |
| 32 | USP44   |                              | 81.2     |
| 33 | USP46   |                              | 42.4     |
| 34 | USP49   |                              | 79.2     |
| 35 | USP51   |                              | 79.8     |
| 36 | UBP1    | USP1                         | 88.2     |
| 37 | UBP2    | USP2, UBP41                  | 41       |
| 38 | UBP3    | USP3                         | 59       |
| 39 | UBP4    | USP4, UNP, UNPH              | 108.6    |
| 40 | UBP5    | USP5, ISOT                   | 95.8     |
| 41 | UBP6    | USP6, TRE2                   | 158.7    |
| 42 | UBP7    | USP7, HAUSP                  | 128.3    |
| 43 | UBP8    | USP8, KIAA0055, UBPY         | 127.5    |
| 44 | VCIP    | VCIP135, KIAA1850            | 134.3    |
| 45 | Cezanne1 |                             | 92.5     |
| 46 | Cezanne2 |                             | 100.7    |
| 47 | A20     |                              |          |
| 48 | UCH-L1  | Park5                        | 24.8     |
| 49 | UCH-L3  |                              | 26.2     |
| 50 | UCH-L5  | UCH-37                       | 37.6     |
| 51 | ATXN3   | ATX3, MJD, MJD1, SCA3        | 43.5     |
| 52 | POH1    | PSMD14                       | 34.6     |
| 53 | CSN5    | COPS5, JAB1                  | 37.6     |
| 54 | SENP1   |                              | 73.4     |
| 55 | SENP2   |                              | 67.9     |
| 56 | SENP3   | SSP3, SUSP3                  | 64.9     |
| 57 | SENP5   | FKSG45                       | 86.7     |
| 58 | SENP6   | FKSG6, KIAA0797, SSP1, SUSP1 | 126.2    |
| 59 | SENP7   | KIAA1707, SSP2, SUSP2        | 112.3    |
| 60 | SENP8   | FKSG8, PRSC2                 | 24.1     |
| 61 | DUB1    |                              | 60.3     |
| 62 | DUB2    |                              | 61.4     |
| 63 | DUB3    |                              | 59.6     |
| 64 | DUB4    |                              | 44.6     |
| 65 | BAP1    |                              | 81       |

Proteolytic enzymes such as isopeptidases play important roles in cell survival, proliferation and differentiation. A mutation in the *Drosophila* FAF (fat facets) gene is believed to increase the number of photoreceptor cells in each facet and to have a maternal effect on embryogenesis. See, Huang, et al. (1995). FAF was described as encoding a USP that is required for negative regulation of neuronal cell determination in the developing compound eye. In addition, FAF is thought to deubiquitinate and stabilize LQF. See, Chen, et al. (2002). The yeast DOA4 gene encoded de-ubiquitinating enzyme is believed to interact with proteasomes, and cleave Ub from conjugated proteins just before they are destroyed by the proteasome, thus recycling Ub. Consistent with this is the major biochemical phenotype of DOA4 negative cells, i.e. a decreased content of free and conjugated Ub. Mutant cells have multiple defects, including slow growth and abnormal DNA repair. See, Papa and Hochstrasser (1993; Papa, Amerik et al. (1999). Human USP-M is though to be associated with chromosomes, phosphorylated at the onset of mitosis, and de-phosphorylated during the metaphase/anaphase transition. See, Cai, et al. (1999). The enzyme is thought to de-ubiquitinate histones and affects chromatin condensation, and appears to play an important role in apoptosis. See, Mimnaugh, et al. (2001). DUB-1 and DUB-2 were identified during the analysis of cytokine-stimulated lymphocytic cell proliferation. High level expression of these genes may result in cell cycle arrest. In fact, DUB-1- and DUB-2 may regulate the degradation rate of critical growth regulator(s). See, Zhu, et al. (1996); Zhu, et al. (1997). USP7 appears to interact with the non-specific transcription activator Vmw110, and has also been described as an enzyme, HAUSP, that deubiquitinates and stabilizes the tumor suppressor p53. See, Everett, et al. (1997); Li, et al. (2002); Wood (2002). The murine Unp gene has been described as a proto-oncogene, and its over-expression in NIH3T3 cells resulted in transformation. See, Gupta, et al. (1994). In a study of primary human lung tumor tissue, human UNP was shown to have elevated gene expression levels and, therefore to have a causative role for this USP in neoplasia. See, Gray, et al. (1995). In cell lines, UNP protein levels were shown to be reduced, therefore indicating that UNP is a tumor suppressor gene. See, Frederick, et al. (1998). The over-expression of the tumor suppressor gene PTEN was shown to up-regulate human UNP. See, Hong, et al. (2000).

Inhibitors of DUBS have characteristic developmental expression patterns, biochemical properties, cellular localization patterns, tissue distributions, preferred targets, and cellular functions. See, Park et al. (2000); Layfield et al. (1999); Cai et al. (1999); Lin et al. (2000); Gong et al. (2000); Park et al. (2000); Hemelaar et al. (2004); Wilkinson (2000); Lin et al. (2001); L1 et al. (2002); Hochstrasser (1996); Chung and Baek (1999); Weissman (2001). The following groups of USP substrates have been thoroughly described: Ub precursors, e.g. naturally occurring fusions of Ub with ribosomal proteins; Conjugates with mono-ubiquitinated proteins, i.e. proteins not destined for proteasomal degradation but, rather, conjugated by Ub to modify various biochemical properties of the protein, e.g. complex formation or cellular trafficking; mis-ubiquitinated proteins, e.g. editing; Poly-ubiquitinated proteins docked to the proteasome, e.g. Ub recycling; and Poly-ubiquitin chains, e.g. monomer disassembly and recycling. Moreover, the ubiquitin-proteasomal pathway has recently been validated for drug discovery. The proteasome inhibitor recently approved for multiple myeloma, Velcade, selectively inhibits the growth of several types of cancer cells (Almond and Cohen 2002; Shah, Potter et al. 2002) (Adams 2002) and has achieved clinical responses (Adams 2002; Adams 2002; Adams 2002). The details of Velcade's therapeutic effect remain to be fully elucidated, but it appears to induce apoptosis with selectivity toward cancer cells. Nevertheless, its efficacy will likely be limited by toxicities, which negatively impacted patient compliance in clinical trials (Adams 2002).

The present invention provides a means for improvement in the selection of compounds with a better therapeutic index, which compounds' activities are associated with the ubiquitin-proteasome pathway, such as USPs and UCHs inhibitors. In one embodiment, the present invention selectively targets ubiquitin metabolism paths as a more selective and effective means than inhibiting all protein degradation as in the case of Velcade®. Ubiquitin-like proteins and ubiquitin are increasingly being implicated in or associated with disease. For example, neurodegeneration was exacerbated by SUMO addition to a pathogenic fragment of the Huntingtin (Htt) pathogenic protein Httex. See, Steffan et al. (2004). The inventors have concluded based on this and other data that a SUMO hydrolase enzyme activator will have therapeutic utility in Huntington's Disease.

Methods of the Invention

The assay described in this patent employs any agent or "reporter", e.g. enzyme, protein, and the like, that requires a free N-terminal amino acid residue for producing a signal, e.g. activity. This agent is inactivated by fusion through its N-terminus to the C-terminus of another protein. By means of example, protease enzymes such as the trypsin family, e.g. factor X, require a free N-terminal lysine to participate in active site peptide cleavage. The assay of the invention further involves a proteolytic enzyme, e.g. an UBL hydrolase, and forms an UBL-reporter fusion protein, which will be cleaved by the proteolytic enzyme. This cleavage of the fusion protein frees both the Ubiquitin and Ubiquitin-like protein (collectively referred to as UBL) or a binding functional fragment thereof possessing a free C-terminus, and the "reporter" with a free N-terminus. In different embodiments of the present assay both the UBL and the reporter now in their active form may be detected by a variety of means known in the art, e.g. with the aid of radioactive, chromogenic, florescent, phosphorescent, chemiluminescent, and other labels and/or substrate. The assay may be conducted with the aid of microtiter plates in which the reaction takes place. In another embodiment of the method of the invention designed for screening of proteolytic enzyme modulators each compound may be added to a microtiter well, preferably prior to other components of the reaction mixture. When compared to a control where cleavage is complete, a screening positive or "hit" will be recognized by a loss of signal, e.g. color or fluorescence, indicating that less UBL or reporter have been freed. In one embodiment where the fusion polymer is a fusion protein, the N-terminus of the reporter protein may be fused to the C-terminus of any of a variety of UBLs or fragment thereof, which will be recognized and cleaved by a proteolytic enzyme, e.g. hydrolase such as a protease or de-ubiquitinase. In another embodiment the assay of this invention may be conducted with different sources of proteolytic enzyme, e.g. purified hydrolases, cellular lysates or extracts from which the enzyme activity must be purified. In another embodiment, the method of this invention may be applied to the discovery of new proteolytic enzymes from a variety of organisms, by substituting different suspected sources of proteolytic enzyme and testing its effect on the fusion polymer, e.g. fusion protein.

In a further embodiment of the assay of the invention, the agent or reporter may be an inactive precursor protein that is fused to a UBL or active fragment thereof. In this embodiment, cleavage of the fusion protein resulting in protein activation, which could generate a positive signal based on the activity of the protein, leading to the production of an end-point associated signal, e.g. a chromogenic end-point. Examples of such precursors are zymogens e.g. fibrinogen and plasminogen, clotting factors e.g. prothrombin, and viral polyproteins e.g. human rhinovirus and poliovirus, among others. In the last example an isopeptidase mediates cleavage of a giant polyprotein containing poliovirus RNA-dependent RNA polymerase (3Dpol) in $E.\ coli$. This is possible because RNA-dependent RNA polymerase requires a free N-terminus for activity, and this activity is easily assayable or detectable. Accordingly, the poliovirus system may be employed in the present assay to assess ubiquitin isopeptidase activity because the activities of RdRp and isopeptidase may be coupled.

As long as a cell encodes a proteolytic enzyme as required by the present invention, e.g. an isopeptidase or a hydrolase (protease), among others known or to be described by the art. These enzymes specifically recognize the UBL sequence and cleave at the junction between the UBL C-terminus and the reporter's N-terminus to generate a free reporter N-terminus, the reporter is or may be thus activated, which will result in a registrable or detectable signal. Any and all reporter enzymes that fulfill the above stated requirements are suitable for use in the assay of this invention. Examples of reporter enzymes are provided in Table 2 below for illustrative purposes only.

TABLE 2

Enzymes Requiring a Free $NH_2$-terminus for Activity

| Protein Family | Specific Examples |
| --- | --- |
| Serine Proteases | Thrombin, Dipeptidyl Peptidases, HtrA2 |
| Prohormone Precursors Subtilisin/kexin-like Prohormone Convertases | Neurophysin, Vasopressin Furin |
| Carboxypeptidases | Carboxypeptidase B, Carboxypeptidase Y |
| ADAMTS | vWF-cleaving protease/ADAMTS 13 |
| ADAM | ADAM 1, ADAM 2 |
| Cysteine Aspartases | Caspases |
| Aspartic Proteinases | Pepsin, Renin, Cathepsin D, Mason-Pfizer monkey virus proteinase |
| MMPs | MMP20, MMP26 |
| RNA-dependent RNA polymerases | $3D^{pol}$ |
| N-terminal nucleophile (Ntn) hydrolases | Glycosylasparginase, 20S proteasome □- subunits, Glutamine PRPP amdiotransferase |
| 4-oxalocrotonate tautomerase family | YdcE, YwhB |

TABLE 2-continued

Enzymes Requiring a Free NH$_2$-terminus for Activity

| Protein Family | Specific Examples |
| --- | --- |
| Chorismate synthases | Chorismate Synthase |
| β-lactam acylases | Cephalosporin acylases, Penicillin acalyse |
| Viral Reverse Transcriptases | CaMV Reverse Transcriptase |
| Phospholipases | Phospholipase A$_2$ |
| Sigma Transcription Factors | σ$^k$ |

In general, simple peptide bonds differ from 'isopeptide bonds". Whereas straight peptide bonds have a recurring —NH—CR—CO—NH—CR'CO— structure, where the COOH carbon is at an α position with respect to the NH— carrying carbon. Isopeptide bonds generally have a greater distance between the carbon atom carrying the amino group and the carboxy function, e.g. isopeptide bonds are generated when at least one of the amino acids involved have the amine group in a non-α position, e.g. β, γ, δ, ε, and the like, with respect to the carboxyl group. Examples of the latter are amino acids such as aspartic acid (β position), glutamic acid (γ position), and lysine (ε position). Many peptidases and isopeptidases are able to cleave linear UBL fusions.

In another embodiment, the method of the invention that activates a reporter by exposing its N-terminus may be applied to cells in the construction of a genetic screen. The enzyme Glutamine phosphoribosylpyrophosphate amidotransferase (GPATase) catalyzes the initial step of purine nucleotide biosynthesis, and is the major regulatory enzyme of the pathway. The GPATase gene is encoded by purF locus of E. coli. See Mei and Zalkin (1990). Deletion of this gene retards the growth of E. coli. When exogenous purine is added to the media (adenine) the cell growth is restored. In example number 2, we have demonstrated that GPATase enzyme can be used as an excellent reporter to monitor Ub or UBL isopeptidase activity since generation of free N-terminal Cyc in GPATase is essential for its activity. Similarly, other N-terminal nucleophile (Ntn) hydrolases (See, Table 12) e.g. asparagine synthetase (See, Andrulis I et al (1989)) and glutamate synthetase (See, Oliver et al 1(987)) may also be used with this invention since there their N-terminus is also required for its biological activity.

A biological selection method is included herein where by Ub-GPATase or UBL-GPATase fusion proteins are transferred to a cell line that lacks the purF locus. These strains may be grown in media containing adenine. The same strain may be transformed also with a plasmid(s) expressing a Ub protease, e.g. isopeptidase, or a UBL protease, e.g. isopeptidase. The cells containing dual plasmids can be grown in synthetic media, independent of added adenine. Thus cell growth is governed by the production of active GPATase by Ub or UBL proteases. If a mutant Ub or UBL protease is transformed to a GPATase harboring E. coli strain, the cells will not grow in the absence of adenine, or glutamate or asparagine as is the case for asparagine synthetase and glutamate synthetase respectively. This selection system can be used to clone novel proteases that will cleave Ub-GPATase or UBL-GPATase. Similarly the system may also be used to select an enzyme, e.g. the best enzyme, from an error prone PCR library that cleaves Ub or UBL-fusion proteins to restore growth by generating an active GPATase or another enzyme of choice.

Another embodiment of the process employs the UB/UBL-fusion protein to the assessment of the effect that the N-end amino acid(s) may have in protein function and/or phenotype. See, Bachmair (1968); Bachmair (1989). Synthetic N-terminal ubiquitin fusion proteins undergo rapid cleavage in vivo in eukaryotes to produce proteins with designated N-terminal residues. In general, as stated by the N-end rule, proteins with certain N-terminal residues will be more susceptible to subsequent ubiquitin-mediated degradation. See, Varshavsky (1996). In this particular embodiment the N-terminus of a fusion protein(s) is modified to vary the protein stability and generate different in vivo protein levels and, thereby regulate their phenotypes, e.g. where a cell function is affected by the level of a protein, e.g. in yeast, Ard1 for alpha-factor sensitivity or Ura3 for survival on uracil-deficient media. See, Park et al (1992). The present method is applied to affect in vivo protein levels and phenotypes by means of fusions with N-terminal SUMO, ISG15, or NEDD8. In these examples the fusion proteins will be cleaved in vivo and the freed N-terminal protein residue will determine the level of that protein and hence the phenotype associated with protein (in)stability as established by the N-end rule. Specific protein residues may be selected for designing fusion constructs in accordance with this invention that will generate a desired protein level(s), e.g. an arginine for destabilization, a methionine for stabilization, or another residue appropriate for the desired level of stability in the type of organism used.

Yet another embodiment of the method of this invention employs a fusion protein including a reporter(s) suitable for optical imaging associated with in vivo proteolytic enzyme, e.g. isopeptidase, activity. By means of example, deubiquitinating enzymes are employed here as a tool in tumor detection employing near-infrad (near IR) optical imaging of protease activity with the aid of contrast agents that fluoresce only after interaction with specific enzymes as described by Weissleder (1999), the relevant text of which describing the process and contract agents being incorporated in its entirety herein. One such proteinase, Cathepsin D, upon cleavage of a dormant or inactive fluorochrome, may release and, thus, activate a fluorochrome by severing the intramolecular optical fluorescent quenching. See, Ching-Hsuan Tung et al. (1999). Ubiquitin and/or UBLs, thus, serve as to reinforce the intramolecular optical fluorescent quenching from fluorochromes on a detection probe that may be used to assay in vitro, ex vivo and/or in vivo for deubiquitinating enzymes and pinpoint activated and/or inhibited activity. The use of Ubiquitin and UBL fluorescent probes is important for early tumor detection and as a follow-up test for tracing the efficacy of treatment because several proteolytic enzymes, e.g. isopeptidases, have been associated with specific diseases as described below.

UBLs exhibit significant conservation of their ubiquitin-like structural folds. Their globular structure may be split into halves, i.e. a C-terminal segment and an N-terminal segment. The SUMO molecule, for example has been split. When a reporter protein was fused to the C-terminal half SUMO (CTHS) it was not cleaved by a SUMO protease. However, when the CTHS-reporter fusion protein was mixed with a N-terminal half SUMO (NTHS) the enzyme does cleave the reporter fusion. Thus the reporter signal is observed only when the two halves of SUMO are able to associate. When associated, the structure is recognized by the protease enzyme, which is then able to cleave and generate an active reporter. In one specific application, the split SUMO embodiment of the present assay may be used to detect molecules, e.g. small molecules, such as metabolites, hormones and drugs that bind to specific receptors. Proteases having cleaving specificity for ubiquitin and UBLs are also suitable for use as switches or sensors, for example, where a receptor molecule attached to ubiquitin or a UBL CTHS-reporter is contacted with and binds a hormone, drug, or ligand, among others (collectively referred to as ligands) on the NTHS, and the protein-protein or protein-small molecule interaction leads to rapid cleavage of the active receptor. This embodiment preferably provides two conditions for a ubiquitin and UBL protease to be an effective switch for the ligand (receptor sensor). The ubiquitin or UBL-receptor is cleaved preferably by a protease when the receptor is bound by its ligand, e.g. hormone. The binding of the ligand preferably promotes a change in ubiquitin or UBL structure that promotes the cleavage of ubiquitin or UBL by its protease. The estrogen receptor ligand binding domain (ER-LBD) is an example of such an application. This embodiment, although having broad application, is exemplified here by reference to the estrogen receptor. The estrogen receptor (ER) interacts with high affinity with a co-activator molecule. This interaction, however, is entirely dependent on the binding of the estrogen hormone to the ligand binding domain (LBD) of estrogen receptor (ER). In this embodiment of the present method, the ligand-binding domain of ER is expressed as a fusion polymer (protein) with the N-terminal half of SUMO (NTHS) or any other UBL, and the CTHS is fused to a co-activator portion of protein that has high affinity for the ER. The co-activator-CTHS reporter fusion protein and the ER-LBD-NTHS fusion proteins may be expressed in a cell system, e.g. *E. coli*, and optionally purified. The protein mixture may be incubated then with a test substance in the presence of SUMO protease. When the estrogen hormone binds to its receptor in the ER-LBD-NTHS fusion it promotes the interaction with the co-activator molecule. The resulting complex leads to cleavage of the reporter, which produces or may be made to produce a signal for reporter activity. The ability to amplify the reporter signal by an enzymatic reaction is the underpinning of the development of this estrogen-ER pair sensor. Since the signal is amplified enzymatically, sensors that work by complementation of split UBLs, e.g. SUMO and other UBLs, will detect not only estrogen, but other hormones and metabolites with greater sensitivity than done by a traditional ELISA kits. Co-activators that are dependent on molecular pairs, e.g. hormone dependent co-activators, and ligand-ligand-receptor pairs, e.g. hormone and hormone receptor pairs may be used as sensors for a variety of human receptors, e.g. nuclear receptors, to detect extremely small, e.g. picomolar, quantities of ligands such as estrogen, androgen, thyroid hormone, or 1,25-dihydroxy vitamin D. By the same token, all UBLs that are split into segments anywhere within the loop between the alpha-1 helix and the beta 3 strand, e.g. halves, which have affinity for one another may be used to construct the sensors with the aid of their respective proteolytic enzymes, e.g. hydrolases. The sensor embodiment of the present assay relies on signal production by the generation of a free N-terminus or its coupling to a signal producing event.

Isopeptidase enzymes exist throughout the plant and animal kingdoms, all of which are considered suitable for use with this invention. The yeast SUMO protease enzyme (ULP1), for example, is particularly robust and faithful in its cleavage properties, and has been used in most of the exemplary disclosure provided in this patent. See, for example, Malakhov (2004). This embodiment of the present assay was validated using other known isopeptidases for various UBLs, a requirement being the absolute dependence of a given signal on the generation of a free, un-fused reporter amino terminus, which in this example is generated by the isopeptidase enzyme SUMO protease (ULP1). Any inhibition of the isopeptidase activity afforded by a modulator, e.g. screened compounds, results in attenuation of the enzymatic activity. Other examples of combinations of elements to carry out the assay of the invention listed here are Poliovirus 3D RNA-dependent RNA polymerase fused to SUMO and cleaved with ULP1, Glutamine phosphoribosyl pyrophosphate amido-transferase (GPAT) fused to SUMO and cleaved with ULP1, Tryptase fused to SUMO and cleaved with ULP1, and Phospholipase $A_2$ fused to yeast and human SUMO, Ubiquitin, Nedd8, Rub1, and ISG15 and cleaved with ULP1, Senp2, USP2, Den1, and various cell extracts. These are but mere examples of the numerous combinations suitable for use in the assay and kit of the invention.

The present invention is provided, therefore, in this patent in the form of several major embodiments, which include applications of UBL-reporter fusion polymers to monitoring the activities of Ubiquitin and Ubiquitin-like protein hydrolases, e.g. proteases, UBL-reporter fusion polymers, and signal producing free reporter structures as probes to monitor proteolytic enzymes such as UBL hydrolases, e.g. proteases, and their activities in man and other animals, cells, tissues and cell fractions. Paramount amongst these is the use of UBL-reporter fusion polymers, and the assessment of proteolytic enzyme activity, such as UBL hydrolase, e.g. protease, activities as selectable markers for eukaryotic and prokaryotic organisms. Another important embodiment relies on UBL-reporter molecules, e.g. enzymes, and their chimeric structures as sensors enabled by cleavage with appropriate proteolytic enzymes, e.g. hydrolases and proteases, to detect protein-protein interaction and small molecule-protein interactions. In yet another embodiment, UBL-reporter enzymes are employed in the manufacture of kits for monitoring the activities and assaying for proteolytic enzymes, e.g. UBL hydrolases and proteases. Some of the most preferred embodiments of the present invention use of a variety of "reporter" structures, such as enzymes, polymerases, proteases, lipases, acylases among others, that require specific N-terminal residues for their reporting activity. Other embodiments rely on the expression of fusion polymers, wherein the C-terminus of the UBL is linked to the N-terminus of the reporter in a fusion polymer carrying an inactive form of the reporter, and wherein a free N-terminal reporter structure is generated by action of a proteolytic enzyme, e.g. UBL hydrolase or protease to render the reporter active. The reporter may be enzymes, or other signal producing entities whether by themselves or by interaction with other entities.

Yet another preferred embodiment employs UBL-reporter fusion polymers, e.g. proteins, obtained or expressed in and purified from any source, e.g. *E. coli*, and cleaved, e.g. in vitro, by a proteolytic enzyme such as an UBL hydrolase, protease or isopeptidase to generate active signal producing active reporter or enzyme. The thus produced signal and/or the reporter enzyme activity may be used as a measurable output of the proteolytic enzyme, e.g. UBL hydrolase or protease, activity in a high throughput screening method and kit for identifying modulators of enzyme activity, such as small molecules that inhibit or activate the proteolytic enzyme, e.g. hydrolase or protease. In a further embodiment, proteolytic enzymes such as UBL-hydrolases or proteases may be employed to generate active reporter signals, e.g. signal producing enzymes, in vivo and to develop cell based assays for specific proteolytic enzymes such as UBL hydrolases and proteases. In a most preferred embodiment, UBL-reporter fusion polymers may be employed as transgenic constructs integrated into cell chromosomes for use as sensors to track activity of specific proteolytic enzymes, e.g. hydrolases and proteases, in various organisms, cells, bacteria, fungi, and animal and plant tissues and cell fractions. One other embodiment utilizes UBL-pro-reporter structures, such as pro-enzymes, as affinity agents or matrices for various proteolytic enzymes, such as UBL hydrolases and proteases. In addition, the UBL-reporter fusion structures may be employed in the present assay and kit as tools to uncover novel proteolytic enzyme structures, e.g. UBL domain structures. The present method and kit may be employed also with the aid of mutant or modified Ubiquitin or UBL structures, or binding functional segments thereof, and the corresponding mutant UBL-reporter fusion polymers to discover and invent novel improved proteolytic enzymes, e.g. UBL hydrolases and proteases. In one extremely preferred embodiment of the invention, the assay and kit rely on UBL-reporter fusion structures employed as selectable markers for eukaryotic and prokaryotic growth and/or phenotype detection. A further embodiment provides a method and kit employing UBL-reporter fusion structures as probes to screen for novel UBL-reporter enzymes. These kits will include the UBL-fusions along with other reagents to assay the activity of proteolytic enzymes, such as UBL hydrolases and proteases.

In a different embodiment, this patent provides a method and kit that employs UBL-reporter fusion structures as tools to produce better signaling reporters, e.g. enzymes. Another important embodiment provides a method and kit of the invention that employ a reporter that has a special requirement for its free N-terminus, such as the case of an enzyme, e.g. a tautomerase, which requires proline as the active N-terminus. In this case the methods and kit employ the reporter in UBL-N-proline reporter fusion polymers to discover novel proteolytic enzymes, e.g. hydrolases and proteases that are specific for UBL-proline fusion bonds. This patent provides a clear improvement over the prior art technology in the form of an assay and kit for identifying and assaying "reporter" enzyme(s) that are inactive in their ubiquitin or UBL fused configuration if fused through their N-terminus, and activated upon cleavage by a ubiquitin or UBL protease due to the liberation of their N-termini. Table 2 above lists examples of several classes of reporter enzymes that require a free N-terminus for biological activity. In many cases, the N-terminal residue is part of the catalytic site or is essential to the catalytic mechanism. For these reasons, the fusion of their N-terminus to ubiquitin or UBLs inactivates the enzymes in a reversible manner, while the removal of ubiquitin or UBLs rapidly restores their activity. The generation of an active reporter enzyme is, therefore, a direct function of the respective protease.

In a further embodiment, Ubiquitin and UBL-reporter fusion genes may be transferred to any organism by known means, and optionally integrated into the host's chromosome, to thereby generate transgenic plants and animals. Since many of the enzymes reported in Table 2 have unique substrates, they may be employed in a signal producing assay, e.g. a fluorescence or chromogenic signal, in tissues or cells where such enzymes are present. Thus, UBL-reporters coupled with easily detected substrates serve as novel biochemical and genetic markers, reporting unique activities of proteolytic enzymes, e.g. isopeptidases and proteases, in situ. The Ubiquitin and UBL-fusion genes of this patent are also useful as selectable markers. By means of example, an N-terminal fusion of the *E. coli* glutamine-PRPP-amidotransferase (GPAT) gene that is essential for purine biosynthesis to a Ubiquitin or UBL-fusion gene may be ligated to a vector, e.g. a plasmid, and employed to transfect cells whose chromosomal GPAT gene is deleted or mutated. The GPAT enzyme requires a free N-terminus to be active, Isopeptidase cleavage of the fusion protein, therefore, would be required to restore the de novo purine biosynthetic pathway. Cells harboring such a UBL-marker gene would allow for selection of plasmids carrying the appropriate isopeptidase or protease genes. Thus, the protease gene would act as a switch to activate the protein essential for cell viability. Purified inactive ubiquitin- and UBL-reporter fusion proteins may be employed, for example, for in vitro screening of novel proteolytic enzymes, such as proteases and isopeptidases. The present assay is also suitable for monitoring the activities of a mixture of proteases that display selective cleavage of ubiquitin or Ubiquitin one or more members of the UBL family. A SUMO-X reporter, for instance, may be an excellent substrate for ULP1 (SUMO protease) whereas a SUMO-Y reporter may be a superb substrate for Ulp2, a second, distinct SUMO protease.

More specifically this patent provides in a first aspect of the invention a method for assessing proteolytic enzyme activity that comprises providing a fusion polymer comprising a first polymer that comprises Ubiquitin or a Ubiquitin-like protein (UBL) or a functional C-terminal segment thereof and a second polymer comprising a free N-terminal amino acid required for detection; wherein the first and second polymers are operatively linked to one another through the UBL C-terminus and the second polymer N-terminus;

contacting the fusion polymer with a proteolytic enzyme or a sample comprising or suspected of comprising the enzyme that cleaves at the UBL C-terminus;

detecting a signal associated with either amount or activity of cleaved polymer; and establishing a correlation between the cleaved polymer's signal to the proteolytic enzyme's activity.

In one embodiment, the method described above may be practiced in a variety of forms and for different purposes. The method may also include normalizing each enzyme or sample cleavage signal by reference to 0% and 100% cleavage signals and assigning a proteolytic enzyme activity value to each enzyme or sample thereof; wherein when the enzyme activity obtained is below a cut-off value it may be said that the enzyme or sample is inactive and when it above the cut-off value it is active. The 0% and 100% cleavage signals may be obtained by methods known in the art, one being by repeating the contacting, detecting and establishing steps for full cleavage and full inhibition of proteolytic enzyme activity to obtain the 100% and 0% cleavage signals. The normalizing step is typically conducted by normalizing each enzyme or sample cleavage signal by reference to a curve of enzyme activity cleavage values and assigning a proteolytic enzyme activity to each enzyme or sample thereof; wherein when the enzyme activity obtained is below a cut-off value it may be said that the enzyme or sample is inactive and when it above the cut-off value it is active. Although other means of normalizing for a blank and/or control, and the like are also contemplated. In another preferred embodiment, the first polymer may comprise the proteins ubiquitin, SUMO, Nedd8, ISG15, Apg8, Apg12, FAT10, Urm1, Hub, UBi, Rub1, ISG15, among many others, or a binding functional C-terminal segment thereof comprising an amino acid within UBL's loop linking its α-helix 1 and β-strand 3 to the C-terminus. In another embodiment the second polymer may comprises a variety of different constructs, amongst the most preferred being a reporter protein or enzyme, transcription factor or signaling functional fragment thereof, and/or the first polymer may comprise a UBL, i.e. Ubiquitin or a Ubiquitin-like Protein, or a binding functional C-terminal segment thereof comprising an amino acid within UBL's loop linking its α-helix 1 and β-strand 3 to the C-terminus. In one form of the method either the first or the second polymer, or both, become(s) detectable upon proteolytic enzyme cleavage. The first and/or second polymer(s) may become(s) detectable by activation of a signal it (they) carry(ies) and/or by binding to or generating a detectable signal. Typically, the signals are a radioactive, fluorescent, phosphorescent, chromogenic, sonogenic, or chemiluminescent signal. However, any other type is also within the confines of this patent. In a particularly preferred embodiment, the method may also include obtaining a UBL N-terminal segment comprising an amino acid within UBL's loop linking its α-helix 1 and β-strand 3 to the C-terminus, or the remainder amino acid segment to form a UBL with the UBL C-terminus segment; the UBL N-terminus segment being operatively linked to one of a first and second binding partners; and obtaining the second binding partner. In this form the fusion polymer is typically cleaved upon binding of the first and second binding partners, which comprise preferably a receptor and a receptor binding agent. Other receptor binding agents may comprises a drug, hormone, an antigen, a ligand, or receptor binding functional fragment thereof; while the corresponding receptor may comprises a drug receptor, hormone receptor, an antibody, a ligand binding receptor, or binding functional fragment thereof. In this embodiment the binding of the UBL N- and C-termini enable recognition of a UBL conformation and polymer cleaving at the C-terminus by the proteolytic enzyme. Of particular importance is a form of the method in which the first and second polymers are covalently linked to one another. In another the first and second polymers are typically operatively linked to one another through a linker, which may comprise at least one amino acid. A most preferred embodiment of the method the fusion polymer comprises a fusion protein, and the proteolytic enzyme typically comprises an isopeptidase or a cleaving functional fragment thereof.

Examples of proteolytic enzymes are a ubiquitin C-terminal hydrolase and a ubiquitin-specific protease or cleaving functional fragment thereof. Other examples amongst the many are constructs that comprise one or more cleaving functional enzymes such as ULP1, ULP2, SENP1, SENP2, yeast YUH1, mammalian UCHL1, UCH-L3, UCH37, Bap1, USP-M, DUB-1, DUB-2; USP7, UNP, CYLD, CYLD1, KIAA0849, USP9X, DFFRX, USP9, FAFX, USP9Y, DFFRY, USP10, FAFY, OTUB1, OTB1, OTU1, HSPC263, OTUB2, C14orf137, OTB2, OTU2, USP10, KIAA0190, USP11, UHX1, USP12, UBH1m, USP12L1, USP13, ISOT3, USP14, TGT, USP15, KIAA0529, USP16, UBPM, USP18, UBP43, USP19, KIAA0891, ZMYND9, USP20, KIAA1003, LSFR3A, USP21, USP23, NEDD8-specific protease, USP22, KIAA1063, USP24, KIAA1057, USP25, USP26, USP28, USP29, USP30, USP32, USP33, KIAA1097, VDU1, USP35, KIAA1372, USP34, USP36, KIAA1453, USP37, KIAA1594, USP38, KIAA1891, USP40, USP42, USP44, USP46, USP49, USP51, UBP1, USP1, UBP2, USP2, UBP41, UBP3, USP3, UBP4, USP4, UNP, UNPH, UBP5, USP5, ISOT, UBP6, USP6, TRE2, UBP7, USP7, HAUSP, UBP8, USP8, KIAA0055, UBPY, VCIP, VCIP135, KIAA1850, Cezanne1, Cezanne2, A20, UCH-L1, Park5, UCH-L3, UCH-L5, UCH-37, ATXN3, ATX3, MJD, MJD1, SCA3, POH1, PSMD14, CSN5, COPS5, JAB1, SENP1, SENP2, SENP3, SSP3, SUSP3, SENP5, FKSG45, SENP6, FKSG6, KIAA0797, SSP1, SUSP1, SENP7, KIAA1707, SSP2, SUSP2, SENP8, VCIP, VCIP135, KIAA1850, A20, UCH-L1, Park5, UCH-L3, UCH-L5, UCH-37, ATXN3, ATX3, MJD, MJD1, SCA3, POH1, PSMD14, CSN5, COPS5, JAB1, SENP1, SENP2, SENP3, SSP3, SUSP3, SENP5, FKSG45, SENP6, FKSG6, KIAA0797, SSP1, SUSP1, SENP7, KIAA1707, SSP2, SUSP2, SENP8, FKSG8, PRSC2, DUB1, DUB2, DUB3, or DUB4, or cleaving functional fragments thereof. Although several examples have been provided, many others known in the art, and that will be uncovered are also suitable as long as they exhibit the required characteristics.

The method of this invention may be practiced with a second polymer comprising a "reporter" or signal producing construct comprising an enzyme such as serine protease, pro-hormone precursor, subtilisin/kexin-like pro-hormone convertase, carboxypeptidase, A Disintegrin-like And Metalloprotease domain (reprolysin-type) with ThromboSpondin type I motif (ADAMTS), A Disintegrin and Metalloprotease Domain (ADAM), cystein aspartase, aspartic proteinase, Matrix Metalloproteinase (MMP), RNA-dependent RNA polymerase, N-terminal nucleophile (Ntn) hydrolase, 4-oxalocrotonate tautomerase, chorismate synthase, β-lactam acylase, reverse transcriptase, phospholipase, transcription factor, or a binding and signaling functional fragment thereof. Other examples are those where the second polymer comprises a viral reverse transcriptase, sigma transcription factor, Glutamine phosphoribosylpyrophosphate (PRPP) amidotransferase (GPATase), coagulation factor Xa, 3Dpol RNA-dependent RNA polymerase, glutamine 5-phosphoribosyl-1-pyrophosphate amidotransferase, penicillin acylase, reverse transcriptase, chorismate synthase, tryptase, chymase, enterokinase, transcription factor $\sigma^k$, thrombin, dipeptidyl peptidase, HtrA2, neurophysin, vasopressin, furin; carboxypeptidase B, carboxypeptidase Y, vWF-cleaving protease/ADAMTS 13, ADAM 1, ADAM 2, caspase, pepsin, rennin, cathepsin D, Mason-Pfizer monkey virus proteinase, MMP20, MMP26, glycosylasparginase, 20S proteasome β subunit, glutamine PRPP amidotransferase, YdcE, YwhB, cephalosporin acylase, CaMV reverse transcriptase, phospholipase $A_2$, or a binding and signaling functional fragment thereof.

The method of this invention may also be practiced by further expressing a polynucleotide encoding the fusion protein under conditions effective for expression thereof as a means for providing the fusion protein in situ. Such polynucleotide may be expressed in a prokaryotic as well as a eukaryotic cell or in a tissue or fraction or extract thereof. In this form, the thus obtained fusion protein may be isolated, and optionally purified prior to the enzyme assay. Moreover, the method may further comprise repeating the contacting, detecting and establishing steps in the presence of a sample suspected of comprising a proteolytic enzyme activity modulator, and determining a value for the effect of the sample on the proteolytic enzyme activity by reference of the sample signal to the corresponding enzyme activity signal obtained in the absence of sample. The sample subjected to the assay typically comprises a physiological fluid, a tissue sample, cell, cell fraction, or extracts or fractions thereof. Clearly, one or more of the steps may be conducted in vitro, in vivo, ex vivo, in cell or tissue culture, on cell or tissue extracts of reaction, among others. Although various signals and detection methods may be employed, common are the detection of cell growth, or the use of chromogenic, radioactive, fluorescent, phosphorescent or chemiluminescent signals. The contacting, detecting, establishing and determining steps may be conducted separately for a plurality of samples suspected of comprising a proteolytic enzyme activity modulator to obtain a value for the effect of the sample on the proteolytic enzyme activity, and the method may even be automated. In the latter mode the collection, processing and reporting of information obtained for each sample and controls may be computerized. The texts of the U.S. Provisional Application 60/580,900 and of the WO 03/057174 A2 and WO 2005/003313 A2 publications are incorporated by their entireties into this patent to provide sources, methods of preparation, examples, and other conditions and elements suitable for enablement of products, their parts and processes employed in the present invention.

As described above, the method of this invention may be applied to assessing the presence of, or uncover, a variety of proteolytic enzymes, modulators, and other regulators in vivo in a plant or animal model. For this purpose, the inventors have designed a transgenic cell, plant or animal, comprising a Ubiquitin- or UBL-reporter fusion gene that is optionally integrated into the cell, plant or animal's chromosome. In another embodiments the fusion polynucleotide may comprise a polynucleic acid that encodes a C-terminal segment of Ubiquitin or a UBL having the characteristics described above. In another embodiment, the "switch and sensor"-mode of the invention may also be incorporated into this aspect. The fusion gene may be constructed either as described elsewhere in this patent or by any of several methods known in the art. See, Sambrook, et al. (1989). It may be then cloned into a vector, e.g. a plasmid and transfected into a cell, plant or animal.

Also provided in this patent is a kit for assessing proteolytic enzyme activity, which kit in its bare bones form comprises a fusion polymer comprising a first polymer that comprises Ubiquitin or a ubiquitin-like protein (UBL) or a C-terminal segment thereof and a second polymer comprising a polypeptide requiring a free N-amino acid terminus for detection; wherein the first and second polymers are operatively linked to one another through the Ubiquitin or UBL C-terminus and the second polymer N-terminus; and instruction for conducting the proteolytic enzyme assay, detecting a signal associated with the amount or activity of the first and/or second polymers, and establishing a correlation of the detected signal to the enzyme's proteolytic activity.

The kit may optionally include a source of a proteolytic enzyme that cleaves at the UBL C-terminus, or the enzyme may be purchased separately. Similarly, another feature of the kit may be the incorporation of plastic ware, reagents, and the like, for practicing the assay of the invention. The kit may additionally include one or more of first and second binding partners, wherein the first partner may be operatively linked to a UBL N-terminus segment, and wherein when the first and second binding partners bind to one another the UBL C-terminal segment binds to the UBL N-terminal segment enabling a UBL conformation, the proteolytic enzyme cleaves the fusion polymer;

reagents for conducting the enzyme cleavage step;

means for conducting the detecting step; and means for correlating the detectable signal to the proteolytic enzyme activity or change thereof.

In this form of the kit the fusion polymer typically includes a fusion protein, or in the alternative a fusion polynucleotide encoding the fusion protein, and optionally one or more reagents for expressing the polynucleotide and/or a cell(s) or fraction or extract thereof for expressing the polynucleotide when employed instead of the fusion protein. A more complete form of the kit may contain means for separately containing a plurality of samples, and instructions for conducting the assay automatically. In this form the kit incorporates means for automatically processing data for each sample, and instructions for its use.

Another application of the present invention is in a method for screening compounds for their effect on proteolytic activity, and the method may be practiced by obtaining a fusion polymer comprising a first polymer that comprises Ubiquitin or a ubiquitin-like protein (UBL) or a binding functional C-terminal segment thereof and a second polymer comprising a free N-terminus amino acid; wherein the first and second polymers are operatively linked to one another through the N-C-termini;

contacting the fusion polymer with a UBL C-terminus cleaving proteolytic enzyme under conditions effective for cleavage to occur, detecting a signal associated with an amount of cleavage to obtain a 100% cleavage signal;

repeating the contacting and detecting steps in the presence of a full inhibitor of proteolytic enzyme activity to obtain a 0% cleavage signal;

obtaining a set of compounds;

separately repeating the fusion polymer obtaining, contacting and detecting steps in the presence of each compound to obtain a cleavage signal;

normalizing each compound cleavage signal by reference to the 0% and 100% cleavage signal and assigning a proteolytic enzyme activity value to each compound.

The method described above may be practiced by conducting the contacting and detecting steps with a known proteolytic enzyme activity modulator to obtain a one-point cleavage control signal instead of the 0% and 100% cleavage signals;

determining a proteolytic enzyme activity value for the modulator by reference to the corresponding enzyme activity value obtained in the absence of the modulator; and normalizing each compound's cleavage signal by reference to the control cleavage signal and assigning a proteolytic enzyme activity value to each compound.

Such modulator typically comprises a proteolytic enzyme activity activator or inhibitor. In this form of the method one or more of the steps may be conducted in vitro, in vivo, ex vivo, in cell or tissue culture, on cells or on tissue fractions or extracts. Some of the parameters that may be observed for detection include cell growth, or chromogenic, radioactive, fluorescent, phosphorescent, sonogenic, or chemiluminescent detection signals.

In one embodiment of this method the normalizing step may be conducted by normalizing each compound cleavage signal by reference to a curve of enzyme activity cleavage values and assigning a proteolytic enzyme activity to each compound; wherein when the enzyme activity obtained is below a cut-off value it may be said that the compound is inactive and when it is above the cut-off value it is active. In this mode, the cut-off value may be selected to be 50% proteolytic enzyme activity, and when the enzyme activity in the presence of the compound is decreased by at least 50% it may be said that the compound is an inhibitor, and when the enzyme activity is enhanced by at least 50% that the compound is an enhancer. Further, the method may include determining a compound's concentration that inhibits ($IC_{50}$) and/or enhances ($EC_{50}$) the enzyme activity by 50%, and comparing the compound's $IC_{50}$ and/or $EC_{50}$ to assess its enzyme activity strength as an inhibitor and/or enhancer. This form of the method may be applied to a library of compounds, and all $IC_{50}$ and/or $EC_{50}$ compared to assess the relative strength of the compounds with respect to one another. As described earlier, the first polymer generally comprises ubiquitin, SUMO, Nedd8, ISG15, Apg8, Apg12, FAT10, Urm1, Hub, UBi, Rub1, ISG15, or a binding functional C-terminal segment comprising an amino acid within UBL's loop linking its α-helix 1 and β-strand 3 to the C-terminus. The latter is particularly useful in the "switch and sensor" mode of the invention, also employing the N-terminal segment of the proteins, which typically may be bound to one of a binding pair, the second member of the binding pair may be bound to a co-activator that facilitates the release of the N-terminal segment for binding to the corresponding C-terminal segment upon binding of the pair members to one another as described elsewhere in this patent. The remaining elements for practicing this form of the method of this invention are as described above, and need not be repeated for this particular application.

In this form the method further includes obtaining a binding functional N-terminal UBL segment comprising an amino acid within UBL's loop linking its α-helix 1 and β-strand 3 to the N-terminus thereof, wherein when the N-terminal segment and the C-terminal segment are bound to one another they form a complete UBL, and the UBL N-terminus segment being operatively linked to one of a first and second binding partners and, as described, obtaining the second binding partner; wherein the fusion polymer, e.g. protein, is cleaved typically upon binding of the first and second binding partners, whether or not aided by a co-activator. As described previously, this form of the assay may also be practiced by obtaining the fusion protein by expression of a polynucleotide encoding it in situ, whether in a prokaryotic or eukaryotic cell or a transgenic plant or animal model transformed with the fusion polynucleotide described above. The thus obtained fusion protein may be isolated, and optionally purified. This form of the method may also be automated, and the collection, processing and report producing on information obtained for each modulator and controls are undertaken in computerized form by means of appropriate software that is commercially available, or may be designed without major complexity.

The method described above may be practiced with the aid of a proteolytic enzyme activity modulator screening kit, which may comprise a fusion polymer comprising a first polymer that comprises Ubiquitin or a ubiquitin-like protein (UBL) or a C-terminal segment thereof and a second polymer comprising a polypeptide requiring a free N-amino acid terminus for detection; wherein the first and second polymers are operatively linked to one another through the Ubiquitin or UBL C-terminus and the second polymer N-terminus; and instruction for conducting the proteolytic enzyme assay, detecting a signal associated with the amount or activity of the first and/or second polymers, and establishing a correlation of the detected signal to the enzyme's proteolytic activity for a plurality of modulators and controls; and optionally a source of a proteolytic enzyme that cleaves at the Ubiquitin or UBL C-terminus.

This form of the kit may also be provided with one or more of first and second binding partners, wherein the first partner may be operatively linked to a UBL N-terminus segment, and wherein when the first and second binding partners bind to one another the UBL C-terminal segment binds to the UBL N-terminal segment enabling a UBL conformation, the proteolytic enzyme cleaves the fusion polymer; reagents for conducting UBL C-terminus enzyme cleavage of the fusion polymer; means for detecting a signal(s) emitted by the first and/or second cleaved polymers; and means for correlating the detectable signal(s) to proteolytic enzyme activity or change thereof by reference to a control. A preferred form of the kit is that where the fusion polymer comprises, or is, a fusion protein, with the kit further comprising a fusion polynucleotide encoding it is substituted for the fusion polymer, and optionally one or more of reagents for polynucleotide expression, and/or a cell(s) or fraction or extract thereof for expressing the polynucleotide when employed instead of the fusion protein. A particularly important form the kit also incorporates means for separately containing a plurality of samples, and instructions for conducting the assay automatically, may also contain means for automatically processing data for each sample; and instructions for its use.

A transgenic cell, plant or animal is also provided by this patent, which comprises a Ubiquitin- or UBL-reporter fusion polynucleotide that is optionally integrated into the cell, plant or animal's chromosome; wherein the Ubiquitin or Ubiquitin-specific proteolytic enzyme, e.g. isopeptidase, is associated with a specific disease or condition or a family thereof. The transgenic cell, plant or animal is typically able to express a Ubiquitin- or UBL-Reporter fusion protein associated with a specific disease or condition or a family thereof. It may be obtained by formation of a hybrid vector by cloning of the fusion polynucleotide into a vector, and transfecting the cell, plant or animal with the hybrid vector. In one preferred embodiment the vector comprises a plasmid, and the cell comprises a eukaryotic cell. However, other vectors and types of cells are also suitable, including prokaryotic cells. The transgenic cell, plant or animal of this invention may be further modified to serve as a cell, plant or animal model for a disease or condition. In specific embodiments suitable for diagnosing a specific disease or condition the Ubiquitin or UBL-isopeptidase is associated with an auto-immune, neoplastic, metabolic, vascular, neurodegenerative or other genetic disease or condition, although this is not an all inclusive list. All other diseases known or to be determined to interact with a specific Ubiquitin or UBL-specific isopeptidase to produce a signal are also included in the present application. Specific examples of the diseases and conditions are cancer, e.g. breast, prostate, and cancers associated with von Hippel-Lindau disease which predisposes to a number of cancers such as hemangioblastomas, pheochromocytomas, and cystadenomas as well as other diseases such as lupus, diabetes, IBD, Parkinson's and cardiovascular disease. Examples of isopeptidase/deubiquitinating enzymes associated with disease include the following:

VDU1/2 and Cancer von Hippel-Lindau disease is an hereditary cancer syndrome caused by germline mutations of the VHL gene. See, Sims (2001). It predisposes those with the disease to various tumors, including hemangioblastomas in the CNS and retina, clear cell renal carcinomas, pheochromocytomas of adrenals, pancreatic tumors, cystadenomas of the epididymis, and tumors of the inner ear. See, Li et al (2002); Maher and Kaelin (1997). VHL protein (pVHL) associates with elongin C, elongin B, and cullin-2 to form a complex, VCB-CUL2, which acts as a ubiquitin E3 ligase. See, Lisztwan et al (1999). Because mutated pVHL is associated with malignancies, the ligase can be considered to be a tumor suppressor and its substrates potential oncogenic molecules. Hypoxia-inducible factor (HIF-α), known to be a substrate of VCB-CUL2, plays a role in development of hemangioblastomas, and likely in tumor angiogenesis in general, via VEGF induction see Ohh et al (2000); Tyers et al (1999) and Benjamin et al (1997). Also among its substrates is an ubiquitin isopeptidase, VDU1, found by yeast 2 hybrid screening to interact with pVHL. A highly homologous protease, VDU2, is also known; although it has not been studied in terms of pVHL association, VDU2 has physiologicai substrates in common with VDU1. See, Curcio-Morelli et al (2003). The β-domain region of pVHL, site of naturally occurring mutations, is the locus of VDU1 interaction, and VDU1 may be co-immunoprecipitated in the VCB-CUL2 complex. The ubiquitination and degradation of VDU1 by a pVHL-dependent pathway is abrogated by VHL mutations that disrupt interactions with VDU1. Thus, targeted degradation of VDU1 by pVHL is important in suppressing tumor formation and/or maintenance, and VDU1 may have oncogenic activity that is uncovered in the absence of the functional ligase. VDU1, therefore, is important in neoplastic disease characterized by mutated pVHL (100% of patients with VHL (autosomal dominant) disease), and 50-80% of the far larger number of patients with sporadic renal clear cell carcinoma. See, for example, Stolle et al (1998); Gnarra et al (1994). Inhibition of VDU1 functionally mimics the activity of the wild type tumor suppressor pVHL.

USP7, USP2a and Cancer

Deubiquitinating enzymes may serve to spare certain proteins, or at least prolong their cellular lifetime by removing the initial ubiquitin tag, thereby preventing proteasomal degradation. One such isopeptidase, USP7 also known as HAUSP, is known to stabilize the tumor suppressor p53. See, Li et al (2002). Another isopeptidase, USP2a, has been implicated in the regulation of fatty acid synthase (FAS), a molecular signature of prostate cancer. See, Rossi et al (2003); Agostini et al (2004); Graner et al (2004). USP2a is androgen-regulated and over-expressed in prostate cancer, and is thus an oncogenic protein. Thus, depending on the roles of their substrates, deubiquitinating enzymes can be either activated or inhibited to achieve therapeutic effect.

Isopeptidase T and Cardiovascular Disease

The de-ubiquitinating enzyme Isopeptidase T is down-regulated in patients with chromosome 22q11 deletion syndrome, which encompasses a variety of heart defects. See, Yamagishi et al (1999). Along with UFD1, isopeptidase T is down-regulated in myocytes from patients with heart failure. See, Kostin et al (2003).

This isopeptidase is known to remove polyubiquitin chains from ubiquitin-protein conjugates and stimulate protein degradation, and its absence results in accumulation of polyubiquitinated proteins and a disruption of the ubiquitin-proteasome degradation pathway, thereby leading to autophagic cell death. See, Hadari et al (1992); Johnson et al (1995); Stefanis et al (2001).

JAMM Motif Isopeptidase AMSH and Pulmonary Disease and Cancer

A JAMM domain-containing protein is linked with the signal transduction associated with endosomal sorting, i.e. trafficking between the membrane and endosomalaysosomal compartments, of the EGF receptor (EGFR). This protein, AMSH (Associated Molecule with the SH3-domain of STAM, a protein that regulates receptor sorting at the endosome). See, McCullough et al (2004); Clague and Urbe (2001). The EGFR regulates numerous cellular functions by initiating signal transduction cascades. See, Lockhart and Berlin (2005); von Ahsen and Bomer (2005); Le Roy and Wrana (2005); Spano et al (2005). During the cellular lifetime of the EGFR, it recycles from membrane to early (sorting) endosome, before finally being selected for sorting to the late endosome and lysosome, where it is degraded by acid proteases. The EGFR participates in signal transduction both at the membrane and in the early endosome compartment. While much of the signaling is concerned with regulation of cell growth and other functions, one component of signal transduction regulates trafficking of the EGFR itself. The E3 ligase Cbl mediates ubiquitination of phosphorylated EGFR. Subsequent signaling events result in degradation of the receptor in late endosomes/lysosomes. Ub-EGFR is recognized by the protein Hrs at the endosomal surface, and further interactions with the endosomal-associated complex required for transport (ESCRT) mediated by ubiquitin result in translocation to internal vesicles of the multi-vesicular body (MVB), committing EFGR to protease degradation in the lysosome. Degradation, the end result of Cbl mediated ubiquitination of EGFR, may be abrogated by a ubiquitin isopeptidase, AMSH, e.g. ablation of AMSH activity by incubation of cells with siRNA leads to increased EGFR degradation; purified AMSH de-ubiquitinates EGFR-Ub in vitro. See, McCullough et al (2004). GFR kinase inhibitors and receptor binding antagonists are currently in clinical trial for various cancers. See, Ciardiello and Tortora (2001); LoRusso et al (2003). Other disease areas with critical unmet needs are also associated with EGFR activity, one being airway inflammation and mucous hypersecretion associated with bronchial asthma. While asthma is a multifactorial disease damage of the bronchial epithelium associated with leukocyte infiltration and increased airway responsiveness are consistent features. See, Puddicombe et al (2000). The EFGR system has been postulated to play important roles in the growth and differentiation of epithelial and connective tissue cell types in the lung. The EGFR and its ligands are elevated during the pathogenesis of asthma, and induction of this system correlates with goblet cell hyperplasia in asthmatic airways. See, Takeyama et al (2001). Any attempted repair of initial epithelial cell damage leads to hyperproliferation and differentiation responses that are linked to EGFR and EGFR activation. See, Bonner (2002). Asthmatics appear to develop chronically high levels of EGFR even in undamaged epithelium. This sustains a constant inflammatory condition, and leads to fibrosis and mucus hypersecretion associated with airway obstruction, morbidity and lethality in asthma, COPD, and other pulmonary diseases.

UCHL1 and Parkinson's Disease

UCHL1, or ubiquitin carboxy terminal hydrolase, is genetically associated with Parkinson's Disease PD). See, Chung et al (2003); Toda et al (2003); Maraganore et al (2004). Mutations in UCHL1 cause autosomal dominant PD, consistent with the notion that derangements in the ubiquitin proteasomal pathway play important roles in the demise of dopanine neurons in PD. Other proteolytic enzymes are associated with other diseases as is known in the art. Various examples are included in Table 3 shown below.

TABLE 3

Deubiquitinating Enzymes Associated with Physiologies, Disease & Enzyme Physiology

| | |
|---|---|
| USP2a | prostatic cancer |
| Ap-UCH | essential for long-term memory in Aplysia |
| BAP1 | tumor suppressor (associates with BRCA1) |
| CYLD1 | tumor suppressor |
| DUB-1 | cytokine-inducible, B-cell selective |
| DUB-2 | cytokine-inducible, T-cell selective |
| D-ubp-64E | *Drosophila* inhibitor of position-effect variegation |
| FAF (Fat facets) | *Drosophila* eye development |
| FAM | pre-implantation mouse embryo development |
| HAUSP (USP7) | tumor suppressor (p53 stabilization) |
| Tre-2 (USP6) | oncoprotein |
| Ubp3 | inhibitor of transcriptional silencing in yeast |
| UBP41 | apoptosis, bone formation |
| UBP43 | negative regulator of IFN signaling, hematopoesis |
| UBP45 | myogenesis |
| UBP69 | myogenesis |
| UbpB (*Dictyostelium*) | developmental timing and spatial patterning |
| UBP-M (USP16) | cell cycle control (chromatin condensation?) |
| UBPY | cell cycle/cell growth |
| USP14 (*ataxia*) | synaptic function |
| UCH-L1 (PGP9.5) | Parkinson's Disease, gracile axonal dystrophy |
| VDU1/VDU2 | tumorigenesis (associates with von Hippel-Lindau protein) |

The hybrid cell, plant or animal of the invention described above may be produced by many methods, including by obtaining a cell, plant or animal;

obtaining a Ubiquitin-, UBL- or their C-terminal binding functional fragment-Reporter fusion polynucleotide;

obtaining a hybrid vector carrying the hybrid polynucleotide operatively linked to a vector; and stably transfecting the hybrid vector into the cell, plant or animal.

In one embodiment the fusion polynucleotide becomes integrated into a cell, plant or animal's chromosome, and becomes fully stabilized. In another embodiment the fusion polynucleotide comprises a fusion deoxyribonucleotide.

The present cell, plant and animal may be employed in diagnosing a disease or condition, for example by obtaining a cell, plant or animal, or fractions or tissue thereof, wherein the Reporter is associated with a disease or condition;

contacting or administering a sample obtained from a subject suspected of being afflicted with the disease or condition with the cell, plant or animal;

detecting any signal produced by the reporter in the presence of the sample; and comparing the signal to controls for 0% and 100% signals, Having now generally described this invention, the same will be better understood by reference to certain specific examples, which are included herein for purposes of illustration only and are not intended to be limiting of the invention or any embodiment thereof, unless so specified.

EXAMPLES

The following examples are illustrative of the present invention and are not intended to be limitations thereon. Unless otherwise indicated, all percentages are based upon 100% by weight of the final composition.

Example 1

Poliovirus Protease

The following example illustrates a preferred isopeptidase assay according to the present invention. The reporter enzyme RNA-dependent RNA polymerase ($3D^{pol}$) requires a free N-terminus for activity. See, Gohara, et al. (1999). The polymerase was fused with Smt3, thereby blocking its N-terminus. When this fusion protein was treated with SUMO isopeptidase a free $3D^{pol}$ N-terminus was generated. Ibid. Gohara, et al. (1999). Subsequent to fusion cleavage, 3Dpol activity can be quantified using a polymerase assay as described below. Thus, isopeptidase-mediated cleavage of poliovirus RNA-dependent RNA polymerase is required in vitro for polymerase activity, and poliovirus RdRp activity is a surrogate measure of isopeptidase activity.

Plasmid Construction, Expression and Purification

An Smt3-$3D^{pol}$ (Mahoney Strain) fusion was constructed, expressed and purified in a manner similar to that described by Malakhov et al. (2004, No. 7}.

Briefly, a poliovirus (Mahoney strain) $3D^{pol}$ gene segment was PCR amplified from the previously described pET26b-Ub-3D-GSSG-6H plasmid described by Gohara et al. (1999) using synthetic primers that incorporate a BsaI site at the 5' end and a BamHI site at the 3' end to facilitate cloning into the pET24-6H-SUMO vector. The primers' sequences were as follows:

```
                                          (SEQ. ID No.: 1)
5'-GCAGGTCTCAAGGTGGTGAAATCCAGTGGATGAG-3'.

(SEQ. ID No.: 2)
5'-GCAGGATCCCTAGTGGTGGTGGTG-3'.
```

The structure of pET24-6H-SUMO-3Dpol, the final construct, was verified by DNA sequencing.

Cleavage Using the Yeast ULP1 Enzyme

A C-terminal His-tagged SUMO protease 1, ULP1 (403-621)p was expressed from pET24d in Rosetta-(DE3) pLysS (Novagen), and purified by Ni-NTA resin. See, Li and Hochstrasser (1999) and Mossessova and Lima (2000). The Ulp and cleavage reactions were completed under standard conditions as described by Malakhov et al. (2004, No. 7}. The reaction was terminated, and the samples boiled for 5 min and subjected to SDS-PAGE. Activity was assessed by quantification of the cleaved fusion by SDS-PAGE. The obtained gels were scanned using Scion Image software to quantitatively assess activity.

3Dpol (polymerase) Activity Assay

The polymerase activity of 3Dpol and its fusion derivative were assayed by either nucleotide incorporation or primer extension. See, Arnold and Cameron (1999). The nucleotide incorporation assay was conducted with radionucleotide with the following reaction mixture: 50 mM HEPES pH 7.5, 10 mM β-mercaptoethanol, 5 mM $MgCl_2$, 60 µM $ZnCl_2$, 500 µM UTP, 0.4 µCi/µL [$\alpha$-$^{32}$P] UTP, 1.8 µM dT15/0.15 µM poly $(rA)_{400}$ primer/template and 3Dpol. All reactions were performed in a total volume of 25 µL using 250 ng of purified 3Dpol at 30° C. for 5 min. The reactions were quenched by addition of 0.5 M EDTA to 83 mM, and 10 µL of the quenched reaction were spotted onto DE81 filter paper discs, and dried completely. The disks were washed then 3 times for 10 minutes with 250 mL of 5% dibasic sodium phosphate and rinsed with absolute ethanol. The radioactivity bound to each filter was quantified by liquid scintillation spectrometry in 5 mL of scintillation fluid. The primer extension reaction contained 50 mM HEPES (pH 7.5), 10 mM β-ME, 5 mM $MgCl_2$, 500 µM ATP, 1 µM sym/sub-U, 0.14 µg/µL of the 3D enzyme and +/−1 µL ULP1 (25 µL total reaction volume).

In Vitro cleavage by ULP1

The Smt3-3Dpol Ulp-1 fusion was incubated under standard conditions for 1, 2, 4, 10, 20, 30, and 60 minutes, and resulted in 100% of cleavage of 3Dpol as confirmed by SDS-PAGE and Coomassie Blue staining. The activity of 3Dpol was assayed by radionucleotide incorporation using the assay described above. The results obtained are shown in Table 4 below.

TABLE 4

$3D^{pol}$ Activity in the Radionucleotide Incorporation Assay

| Time (min) | SUMO-3Dpol | SUMO-3Dpol + Preincubation with Ulp1 | SUMO-3Dpol + Ulp1 in Reaction |
|---|---|---|---|
| 1 | 0 | 12.84 | 2.57 |
| 2 | 0 | 19.69 | 4.96 |
| 4 | 0 | 23.37 | 7.61 |
| 10 | 0 | 33.90 | 20.55 |
| 20 | 0 | 44.61 | 33.59 |
| 30 | 0 | 59.17 | 38.93 |
| 60 | 0 | 67.00 | 54.49 |

As seen in Table 4 above 3Dpol activity was elevated by coincubation of the fusion with Ulp1 and performing the radionucleotide assay and further enhanced by preincubation of the fusion with Ulp1 and subsequently performing the radionucleotide incorporation assay. It is evident from Table X that treatment of the 3Dpol fusion with yeast Ulp1 SUMO protease activates 3Dpol.

Example 2

Glutamine Phosphoribosylpyrophosphate Amidotransferase (GPATase)

This Example illustrates a preferred isopeptidase assay according to the present invention employing GPATase. The enzyme Glutamine phosphoribosylpyrophosphate amidotransferase (GPATase) catalyzes the initial step of purine nucleotide biosynthesis, and is the major regulatory enzyme of the pathway. GPATase transfer the glutamine amide nitrogen (free $NH_3$) to phosphoribosylpyrophosphate (PRPP), yielding phosphor ribosyl amine, pyrophosphate, and glutamate. GPATase belongs to a family of 16 glutamine amido transferases involved in the utilization of the amide nitrogen of glutamine for biosynthetic purposes. See, Zalkin (1993); Tso et al. (1982). *E. coli* GPATase may be either in the form of a tetramer or trimer made up of identical subunits and contains no iron unlike avian, mammalian, or B subtilis GPATase. See, Mantsala and Zalkin (1976). An active site cysteine is required for the transfer of glutamine amide, a critical step of the catalytic mechanism. Since this Cystein is also the N-terminal residue of mature GPATase it is clear that the enzyme requires a free N-terminus for catalytic activity. See, Tso et al. (1982). The reaction is coupled to the reaction $NAD^+$->NADH, which permits the assessment of GPATase activity by measuring the absorption of the NADH reaction product at $\lambda=363$ nm as shown below.

Methods: Plasmid Construction, Expression and Purification of Smt3-GPATase

A Smt3-GPATase fusion was constructed, expressed and purified in a manner similar to that described by Malakhov et al (2004, #7). The *E. coli* purF gene encoding the glutamine phosphor ribosyl pyrophosphate amidotransferase (GPATase) was PCR-amplified employing the pETpurF plasmid described by Bera et al., J.B.C. 275, 7975-7979 (2000) using the following synthetic primers:

```
                                          (SEQ. ID No.: 3)
Forward: 5'-GTCAGGTCTCAAGGTTGCGGTATTGTCGGTATCGC-3'.

(SEQ. ID No.: 4)
Reverse: 5'-GTCAGGATCCTCATCCTTCGTTATGCATTT-3'.
```

These primer sequences incorporate a BsaI site at the 5' end, and a BamHI site at the 3' end of the purF sequence to facilitate cloning into the pET24-6H-SUMO vector. This construct was designed to direct the synthesis of a fusion protein in which the SUMO C-terminal -Gly-Gly amino acid sequence is joined directly to the mature GPATase N-terminus, which is a Cysteine residue at amino acid position 2. The structure of the final construct, pET24-6H-SUMO-GPATase, was verified by DNA sequencing.

Cleavage of SUMO-GPATase Employing the Yeast ULP1 Enzyme

The SUMO protein was cleaved from a SUMO-GPATase fusion protein by treatment with the yeast ULP1 protein (SUMO protease catalytic domain). Approximately 5 µg SUMO-GPATase were incubated at 30° C. for 3 hours with increasing concentrations of the ULP1 enzyme in a reaction mixture containing 50 mM Tris-HCl pH 7.5, 1 mM EDTA, 10 mM DTT. The reaction was quenched by addition of SDS-PAGE sample buffer, heated, and loaded directly on a 12% SDS-polyacrylamide gel, and electrophoresed. After electrophoresis, the gel was stained to visualize the proteins. The SDS-PAGE analysis demonstrated cleavage of the fusion with as little as 0.009 units of Ulp1; however, that cleavage was never fully achieved with as much as 78.3 Units. This inability of the ULP1 enzyme to cut the fusion protein may reflect the occurrence of steric hindrance around the cleavage site, or some partial modification of the junction sequence, e.g. oxidation of the Cysteine residue at the amino-terminal end of GPATase.

In Vitro GPATase Activity Assay

GPATase, a glutaminase enzyme, hydrolizes 5-phospho ribosyl pyrophosphate (PRPP) producing glutamine, 5-phosphoribosyl-(b)1-amine (PRA) and pyrophosphate ($PP_i$). This glutaminase reaction was monitored by measuring the production of glutamate by means of a coupled glutamate dehydrogenase (GDH) assay under standard reaction conditions described by Messenger and Zalkin (1979).

When the fusion protein was incubated for 30 minutes with Ulp1, and the reaction added to the GDH substrate, there was an increase is absorbance at the OD 363 reading, indicative of active Glutamate, which in turn indicates GPATase activity. In the absence of Ulp1, this increase of absorbance did not occur. Furthermore, when increasing concentration of the Smt3-GPATase fusion was increased with increasing Additional experiments described below further quantified and establish this difference between ULP1-cleaved SUMO-GPATase and the untreated fusion protein.

The coupled GDH assay employed to assess GPATase activity was examined for accuracy. Increasing amounts of the purified SUMO-GPATase fusion protein, either untreated or cleaved by the ULP1 SUMO protease, were incubated in the presence of glutamine and PRPP for a fixed period of time, and the completed reaction was then used as substrate in a GDH assay. The results show that there is a linear relationship between the GPATase enzyme concentration and the GDH reaction absorbance read at 363. This is particularly so at enzyme concentrations of 1 µg or less. Thus, the amount of $NAD^+$ reduced in the GDH reaction directly correlates with the amount of active GPATase enzyme in the initial reaction. In addition, treatment with ULP1 results in at least a 10-fold increase in the glutaminase activity of GPATase, despite the fact that only partial cleavage of SUMO-GPATase has been observed thus far.

Example 3

Tryptase Assay

The following example illustrates a preferred isopeptidase assay provided according to the present invention. Tryptases are neutral serine proteases with a molecular weight of 134 kDa. The enzyme is made of 4 non-covalent bound subunits and each subunit has a single active site. There are mainly two members in this family, α-tryptase and β-tryptase with approximately 90% sequence identity between the two. Tryptases are synthesized as inactive precursors, and are stored in secretory granules as active enzymes along with other proteinases. Also, there is a constitutively expressed and secreted version, termed α-protryptase as well. Activation of β-tryptase is a two-proteolytic process whereby the initial cleavage is an autocatalytic intermolecular cleavage that results in a monomer being formed, with a di-peptide at the N-terminus inhibiting the formation of the required tetramer. It is the role of dipeptidyl peptidase I to cleave the di-peptide from the N-terminus allowing the formation of the mature tryptase structure and increasing the activity 50 fold.

Expression of Tryptase Gene Fusions in Insect Cells

Recombinant human tryptase was expressed in a baculovirus (*Autographa californica* nuclear polyhedrosis virus (AcNPV)) insect cell (*Spodoptera frugiperda* (Sf9)) system as described by O'Reilly (1992). The cDNA encoding human typtase was fused in-frame at the 3' end of the sequence coding for either ubiquitin (Ub) or a SUMO, carrying a six histidine residue (6×His) tag at the N-terminus. This hybrid gene was then inserted immediately downstream of the signal sequence for the baculovirus secreted envelope glycoprotein gp67. The expression of the gene fusion was controlled by the polyhedrin p10 or basic protein AcNPV gene promoter. After cloning the gene fusion into the baculovirus transfer vector, the recombinant plasmid carrying the Ub/UBL-tryptase construct was co-transfected with AcNPV baculovirus DNA into insect cells. After several days recombinant viruses that arose by homologous recombination of the transfer vector and the AcNPV deoxyribonucleic acid (DNA) were selected, plaque purified and amplified.

Insect cells infected with the purified recombinant baculovirus are capable of producing milligram quantities of the fusion protein per liter of culture. The Ub/SUMO-tryptase protein was secreted into the medium as an intact fusion protein without the gp67 signal sequence. The presence of the N-terminal 6×His tag facilitated the subsequent purification of the protein on Ni-NTA Agarose (metal affinity chromatography) and the size validated by SDS-PAGE. Upon cleavage with the appropriate isopeptidase, the appropriate dropout bands resulted.

Tryptase Enzymatic Activity Assay

The activity of human Tryptase was measured using either a chromogenic or fluorometric enzymatic assay or both. The purified fusion protein was cleaved by the appropriate UBL hydrolase/protease, which activated tryptase. The tryptase activity was assayed using a peptidyl chromogenic substrate whose hydrolysis was monitored by measurement of changes in absorption at 410 nm. See Schechter et al. (19981998). Upon cleavage of the purified Smt3-tryptase with Ulp1, augmented tryptase activity was measured following the protocol of Schechter and colleagues. Prior to cleavage by isopeptidase, neither the Ubiquitin-tryptase nor SUMO-tryptase had any tryptase activity. Only upon cleavage by isopeptidase did we see tryptase activity. Therefore, the tryptase fusion is a useful tool to identify isopeptidase activity.

Example 4

Phospholipase $A_2$ Assay

The following example illustrates a preferred mode of the assay of the invention employing phospholipase $A_2$. Phospholipases are a family of enzymes that was initially identified in snake venom, and later on found to be conserved throughout higher organisms. Phospholipases are grouped in subfamilies according to their size, pattern of expression and dependence on co-factors. The secreted phospholipase $A_2$ (sPLA$_2$) enzyme subfamily may be differentiated from other PLA$_2$ subgroups, such as cytosolic, intracellular members and $Ca^{2+}$-independent PLA$_2$ is 6 forms in that they are disulfide rich 14-16 kDa proteins that require millimolar concentrations of $Ca^{2+}$ for catalysis See, Gelb (1995). In mammalian systems there are in excess of eleven sPLA$_2$ enzymes, e.g. IB, IIA, IIC, IID, IIE, IIF, III, V, X, XIIA and XIIB. sPLA$_2$ possesses a broad specificity for phospholipids with different polar head groups and fatty acyl chains. The enzymes of the PLA$_2$ family catalyze phospholipid cleavage at the sn-2 position to yield free fatty acids and lysophospholipids. See, Dennis (1994).

sPLA$_2$ enzymes are generated as proenzymes that are catalytically inactive See Dijkstra (1981). Upon secretion and cleavage by processing proteases, such as trypsin, the N-terminal propeptide is cleaved to yield active enzyme with the desired N-terminus. See, Cupillard (1997). It is the free N-terminus that is required for catalytic activity as it is involved in hydrogen bonding and interfacial binding. See, Dijkstra (1984); Yuan, (1999); Grataroli et al (1982).

Ubiquitin/UBL-PLA$_2$mX Plasmid Construction

All plasmid constructs for expression in *E. coli* were derived from the pET24d(+) expression vector (Novagen). The Ubiquitin/UBL-fusion expression vectors were constructed as detailed by Malakov et al (2004). The mouse Group X PLA$_2$ was selected as an example for the whole PLA$_2$ enzyme group. The fusion constructs were made by PCR amplification of the murine PLA$_2$ Group X gene with designed primers that only amplified the processed active Group X PLA$_2$ enzyme form. Included within the 5' and 3' primers were unique BsaI and BamHI restriction sites, respectively. This permitted the insertion downstream of the Ubiquitin/UBL gene, and thereby in frame translation of the fusion protein. The primers used were as follows:

```
                                            (SEQ. ID No.: 5)
Forward: 5'-GATCGGTCTCAAGGTGGACTCCTGGAGCTGGCAGGG-3'.

(SEQ. ID No.: 6)
Reverse: 5'-GATCGGATCCTCAATTGCACTTGGGAGAGTC-3'.
```

Eventually Ubiquitin-PLA$_2$mX, (yeast SUMO) Smt3-PLA$_2$mX, human SUMO3-PLA$_2$mX, ISG15-PLA$_2$mX, human Nedd8-PLA$_2$mX and yeast Rub1-PLA$_2$mX fusions were created employing the same protocol as detailed above. Prior to expression, the expression plasmid was sequence verified for correct in frame translation products.

Expression and Purification of Ubiquitin/UBL-PLA$_2$mX in *E. coli*

The bacterial expression of the Ubiquitin/UBL fusion proteins was performed following transformation into either BL21(DE3) or Rosetta (DE3), two *E. coli* host strains. Soluble and insoluble fractions were deposited, electrophoresed on an SDS-PAGE gel, and stained with Coomassie Blue to verify size and expression of each fusion. Then the Ubiquitin/UBL-PLA$_2$mX was purified from the insoluble fraction by chromatography on NiNTA resin (Qiagen), and dialyzed for 48 hours with buffer exchange. All fractions were collected, and then electrophoresed by SDS-PAGE and stained with Coomassie Blue. Each construct expressed the appropriately sized band as expected, as is shown in Table 5 below.

PLA$_2$ Assay

Phosphotidylcholine with a fluorophore conjugated on the sn-2 position of the lipid was used as a substrate for assaying PLA$_2$ activity. The fluorophore released upon cleavage of the sn-2 acyl bond by active PLA$_2$ was detected at its specific excitation and emission wavelengths. Two fluorophores were used: NDB (ex: 460 nm/em: 534 nm) and BODIPY FL (ex: 503 mm/em: 512 nm) (Molecular Probes/Invitrogen). The lipid substrate was diluted in PLA$_2$ assay buffer (10 mM Tris, pH 8, 100 mM KCl, and 2 mM Ca$^{2+}$) to a final concentration of 5 µm. The cleavage reactions were either performed in a 96 well black plate or in a 1.5 ml Eppendorf tube, and then a lipid substrate was added. Upon addition of cleavage product or ubiquitin/UBL-isopeptidase, 400 millisecond readings were recorded at 15 second intervals for a total of 30 minutes. In another protocol employed a cleavage reaction was assembled in a 96 well plate by adding collectively the PLA$_2$-fusion construct, either a cell extract or isopeptidase, and substrate. Successive readings were taken until a desired time point, such as 30 minutes. Cleavage of the fusions was detected by an increase in fluorescence of the cleaved lipid substrate.

Ubiqutin/UBL-PLA2mX Cleavage with Whole Cell and Plant Extracts

The cleavage of various Ubiquitin/UBL-PLA$_2$ fusions was undertaken with the aid of whole cell extracts. It was determined that this cleavage resulted in the appropriate or expected sized drop-out bands. Two bands were seen on the Coomassie Blue stained gels: a constant 14 kDa PLA$_2$mX band, and the Ubiquitin/UBL fusion partner sized band, whose size depended on the UBL fusion partner. The results obtained are shown in Table 5 below.

TABLE 5

Sizes of Intact Ubiquitin/UBL-fusions & Cleavage Products

|   | Size of Full length UB/UBL-PLA | Cleaved Ubiquitin/UBL | Cleaved PLA$_2$mX |
|---|---|---|---|
| Ubiqutin-PLA$_2$mX | 23.5 kDa | 9 kDa | 14 kDa |
| Yeast SUMO- | 32 kDa | 12 kDa (runs at 21 kDa) | 14 kDa |
| hSUMO3-PLA$_2$mX | 32 kDa | 12 kDa (runs at 21 kDa) | 14 kDa |
| Nedd8-PLA$_2$mX | 24 kDa | 9.7 kDa | 14 kDa |
| Rub1-PLA$_2$mX | 24 kDa | 9.7 kDa | 14 kDa |
| ISG15-PLA$_2$mX | 30 kDa | 15 kDa | 14 kDa |

Each of the cleavage reactions contained 5 µg fusion protein, and a similar amount Insect Cells, Rabbit Reticulocyte Fraction II, human U20S osteosarcoma cells, colon cancer cell lines DLD1 and HCT116, human non-small-cell lung cancer H460 cells, human Embryonic Kidney 293T cells, murine T helper lymphocyte clone, or wheat germ cell extract. The reaction mixture samples were incubated overnight, removed, electrophoresed on a 15% SDS-PAGE gel, and stained with Coomassie Blue for analysis of cleavage. The results are shown in Table 6 below.

TABLE 6

Cleavage Activity Profile of Cell and Plant Extracts

| CLEAVAGE | Ubiquitin-PLA$_2$mX | hSUMO3-PLA$_2$mX | Nedd8-PLA$_2$mX | Rub1-PLA$_2$mX |
|---|---|---|---|---|
| Insect Cell | − | ++++ | + | − |
| Rabbit Reticulocyte | ++++ | +++ | ++ | ++ |
| U20S | − | ++ | + | − |
| DLD1 | ++ | ++ | + | − |
| H460 | ++ | +++ | ++ | − |
| HEK293T | ++ | ++++ | +++ | + |
| L2 | ++ | ++++ | +++ | + |
| HCT116 | +++ | ++++ | ++ | − |
| Wheat Germ | +/− | ++ | +/− | + |

(+/− = <10%; + = 10%-25%; ++ = 25%-50%; +++ = 50%-75%; ++++ = 75%-100%)

Furthermore, the PLA$_2$ assay was performed as described above to measure PLA$_2$ activity using the BODIPY FL labeled lipid substrate described above and represented as a ratio of activity where extracts were added to the fusion protein over the fusion protein by itself. The results are shown in Table 7 below.

TABLE 7

Ratio of PLA$_2$ Activity from Cleaved Fusions by Cell & Plant Extracts

| PLA$_2$ activity | Ubiquitin-PLA$_2$mX | hSUMO3-PLA$_2$mX | Nedd8-PLA$_2$mX | Rub1-PLA$_2$mX |
|---|---|---|---|---|
| Insect Cell | 4.72 | 6.31 | 3.02 | 4.4 |
| Rabbit Reticulocyte | 21.24 | 2.19 | 6.59 | 25.1 |
| U20S | 4.33 | 2.59 | 3.15 | 4.0 |
| DLD1 | 5.95 | 4.52 | 3.73 | 4.8 |
| H460 | 6.34 | 5.90 | 4.19 | 3.6 |
| HEK293T | 5.68 | 3.47 | 6.20 | 4.2 |
| L2 | 8.39 | 5.86 | 5.94 | 3.9 |
| HCT116 | 9.03 | 5.5 | 3.96 | 2.8 |
| Wheat Germ | 1.86 | 157.09 | 20.27 | 95.63 |

As may be seen from the data provided in Table 7 above Ubiquitin/UBL-PLA$_2$mX fusion protein cleavage correlated nicely with PLA$_2$ activity. For ISG15-PLA2mX activity, we used whole cell extracts from HEK293T cells that were transfected to express UBP43, the ISG15-specific isopeptidase. In this assay, ISG15 fusion was incubated with UBP43 transfected extracts and non-transfected control extracts and the cleavage and fluorescent was monitored real time. There was fluorescent activity in both conditions, albeit the PLA$_2$ activity within the UBP43 transfected cell extracts was present prior to that of the untransfected cells. This could be attributed to endogenous, constitutively expressed processing proteases, as ISG15 is initially a 17 kDa precursor that is processed to 15 kDa This processing protease may have some affinity for the ISG15-PLA$_2$ fusion, albeit at a much lower affinity that of UBP43 for ISG15, therefore, the delayed fluorescent readings in the PLA$_2$ assay. Nonetheless, our assay was able to detect UBP activity directed towards the ISG15 fusions. In the presence of UBP43, there is a 4 fold increase in the rate of PLA$_2$ activity, demonstrating the utility of the ISG15-PLA2 fusion to detect ISG15-isopeptidase activity.

Ubiquitin/UBL-PLA$_2$mX Cleavage Using Ubiquitin/UBL-Specific Isopeptidases Yields PLA$_2$ Activity.

In these experiments reporter fusion proteins were incubated in the presence or absence of isopeptidases that target specific Ubiquitin or UBL moieties, and assayed for isopeptidase activity by either monitoring fusion cleavage by SDS-PAGE or by detecting PLA$_2$ activity. Since the yeast Ulp1 isopeptidase has specificity for the yeast Smt3 gene product it was employed for cleavage of a yeast Smt3 fusion protein. Likewise, the SENP2 isopeptidase was used for cleavage of the human SUMO3 fusion protein, and the shared core enzymatic domain of the spliced USP2 product, either USP2a or USP2b. See, Lin et. al. (2000), was used for cleavage of a Ubiquitin fusion protein. And lastly, Den1, a Nedd8-specific isopeptidase was used to cleave a Nedd8-PLA$_2$mX fusion protein. See, Gan-Erdene (2003).

10 µg of yeast Smt3-PLA$_2$mX were incubated with 1 µg Ulp-1 for an hour and analyzed by SDS-PAGE. Analysis of the gel showed complete cleavage of the reporter fusion protein to yield the separate constituents, Smt3 (at 21 kDa) and 14 kDa PLA$_2$mX. When the same experiment was conducted in the absence of ULP1 there was no auto-catalytic activity. Only the intact 32 kDa fusion was seen. The yeast ULP1 enzyme failed to cleave the Ubiquitin-PLA$_2$mX fusion protein in a showed of specificity for the SUMO-fusion protein. When 10 µg hSUMO3-PLA$_2$mX were incubated with 1 µg SENP2, and the samples monitored by SDS-PAGE the appropriately sized hSUMO3 (21 kDa) and PLA$_2$mX (14 kDa) bands were observed, indicating complete cleavage of the fusion protein. The SENP2 enzyme failed to cleave the Ubiquitin-PLA$_2$mX fusion protein, as previously observed with Ulp1, showing specificity of isopeptidase activity for SUMO. When 10 µg of the Ubiquitin-PLA$_2$mX fusion was incubated with 3 µg of the core domain of USP2, complete cleavage of the fused Ub-PLA$_2$mX was seen. No parental (fusion protein) 24 kDa band was seen while the 14 kDa PLA$_2$mX band and the 9 kDa Ubiquitin band appeared. When the Nedd8-PLA$_2$mX fusion protein was incubated with the Nedd8-specific isopeptidase Den1, the Nedd8-fusion protein became cleaved and 14 kDa PLA$_2$mX and 9 kDa Nedd8 bands appear. An in vitro PLA$_2$ assay was performed to assess PLA$_2$mX activity for cleavage of the Ubiquitin/UBL fusion protein by specific isopeptidases. In all cases where co-incubation of the Ubiquitin/UBL-PLA$_2$mX fusion and the specific isopeptidase led to the cleavage and generation of the 14 kDa PLA$_2$mX band, there was heightened PLA$_2$ activity, as visualized by the fluorescence intensity increase. In all instances described above, in which the UBL-specific isopeptidase cleaved the fusion, PLA$_2$ activity was monitored as well and the ratio of PLA$_2$ activity from Fusions incubated with and without UBL-specific isopeptidases are shown in Table 8 below.

TABLE 8

Ratio of PLA$_2$ Activity from UBL-specific Isopeptidases Activity

| Fusion (−/+isopeptidase) | Ratio |
| --- | --- |
| Smt3-PLA2mX | 1 |
| Smt3-PLA2mX + ULP1 | 7.04 |
| hSUMO3-PLA2mX | 1 |
| hSUMO3-PLA2mX + Senp2 | 9.95 |
| Ubiquitin-PLA2mX | 1 |
| Ubiquitin-PLA2mX + USP2 | 9.37 |
| Nedd8-PLA2mX | 1 |
| Nedd8-PLA2mX + Den1 | 3.38 |

This example shows the utility of Ubiquitin/UBL-PLA$_2$ fusion proteins to detect proteolytic, e.g. isopeptidase, activity. In the absence of any isopeptidase activity, fusion protein alone, there is no signal generated. In the presence of cell extracts that contain isopeptidase activity or more specifically, purified recombinant isopeptidases, the fusion protein becomes cleaved and yields a quantifiable level of PLA$_2$ activity.

A large number of enzymes are known that are capable of cleaving ubiquitin or UBLs from their target proteins or linear fusion proteins. Genome sequencing throughout the phylogeny is producing other examples. Up to the present time there existed no straightforward functional assay suitable for rapid, accurate and selective screening of these enzymes or for screening of compounds that modulate their activities. Currently available assays are difficult and require many steps to produce isopeptide-linked substrates containing ubiquitin or UBLs to conveniently assay proteolytic enzyme, e.g. isopeptidase or hydrolase (protease), activities. Although the removal of ubiquitin or UBLs from a target protein in accordance with this invention may be monitored by Western blotting; however, the prior art assays are characterized by low sensitivity and throughput. A UBL such as ubiquitin and UBLs may be fused to a protein domain such as GST, which subsequently may be immobilized on a solid support and cleaved, and one of the products filtered or assayed by a modified high throughput ELISA assay. However, the prior art methods afford relatively low sensitivity, contain multiple steps, and are expensive because they require ELISA reagents. In addition, if, for example, GST-fusions or fusions with any other enzyme were employed the prior art assays would also be prone to artifacts should the protein be recognized by antibodies and/or the enzyme remain active even in a UBL-fused state.

The invention being thus described, it will be obvious that the same may be modified or varied in many ways. Such modifications and variations are not to be regarded as a departure from the spirit and scope of the invention and all such modifications and variations are intended to be included within the scope of the following claims.

The following references are cited as indicative of the general state of the art, and as an aid to understanding the inventive subject matter in its proper context. Citation of a reference in this application is not to be construed as an admission of materiality to patentability of the inventive subject matter, nor as an admission that any such reference is prior art; material references will be cited in an Information Disclosure Statement. All references cited herein and below are hereby incorporated by reference in their entirety herein.

REFERENCES

Adams, J. (2002). "Development of the proteasome inhibitor PS-341." Oncologist 7(1): 9-16.

Adams J. (2002) "Preclin/lin eval of proteasome inhib PS-341 for cancer." Curr Opin Chem Biol 6(4): 493-500.

Adams, J. (2002). "Proteasome inhibition: a novel approach to cancer ther" Trends Mol Med 8(4 Suppl): S49-54.

Almond, J. B. and G. M. Cohen (2002). "The proteasome: target for cancer chemother" Leukemia 16(4): 43343.

Agostini, M., S. D. Silva, et al. (2004). "Fatty acid synthase required for prolif of human oral squamous carcinoma cells" Oral Oncol 40(7): 728-35.

Andrulis, 1. Shotwell, M, Evans-Blackler S. et al (1989) Fine Structure analysis of the Chinese hamster AS gene encoding asparagine synthetase. Gene 80: 75-85

Arnold, J. J., and C. E. Cameron (1999). "Poliovirus RNA-dependent RNA polymerase (3Dpol) is sufficient for template switching in vitro." J Biol Chem 274(5):2706-16

Baek, S. H., K. S. Choi, et al. (1997). "Molecular cloning of a novel ubiquitin-specific protease, UBP41, with isopeptidase activity in chick skeletal muscle." J Biol Chem 272 (41): 25560-5.

Baek, S. H., K. C. Park, et al. (1998). "A novel family of ubiquitin-specific proteases in chick skeletal muscle with distinct- and C-terminal extensions." Biochem J 334 (Pt 3): 677-84.

Bachmair, A., D. Finley, and A. Varshavsky (1986) In vivo half-life of a protein is a function of its amino-terminal residue. Science 234:179-186.

Bachmair, A., and A. Varshavsky (1989) The degradat signal in a short-lived protein. Cell 56:1019-1032.

Baker, R. T., S. A. Smith, et al. (1994). "Protein expression using cotranslational fusion and cleavage of ubiquitin. Mutag of glutathione-binding site of human Pi glutathione S-transf" J Biol Chem 269(41): 25381-6.

Baker, R. T., J. W. Tobias, et al. (1992). "Ubiquitin-specific proteases of *Saccharomyces cerevisiae*. Cloning of UBP2 and UBP3, and functional analysis of the UBP gene family." J Biol Chem 267(32): 23364-75.

Balakirev, M. Y., S. O. Tcherniuk, et al. (2003). "Otubains: a new family of cysteine proteases in the ubiquitin pathway." EMBO Rep 4(5): 517-22.

Brain and Williams (1988) "Subst P reg vasodil act of calcitonin gene-related peptide" Nature 335(6185): 73-5.

Benjamin, L. E. and E. Keshet (1997). "Conditional switching of vascular endothelial growth factor (VEGF) expression in tumors: induction of endothelial cell shedding and regression of hemangioblastoma-like vessels by VEGF withdrawal." Proc Natl Acad Sci USA 94(16): 8761-6.

Bonner, J. C. (2002). "The epidermal growth factor receptor at the crossroads of airway remodeling." Am J Physiol Lung Cell Mol Physiol 283(3): L528-30.

Buchanan, J. M. (1973). "The amidotransferases." Adv Enzymol Relat Areas Mol Biol 39:91-183.

Cai, S. Y., R. W. Babbitt, et al. (1999). "A mutant deubiquitinating enzyme (Ubp-M) associates with mitotic chromosomes and blocks cell division." Proc Natl Acad Sci USA 96(6): 2828-33.

Chen, X., B. Zhang, et al. (2002). "A specific protein substrate for a deubiquitinating enzyme: Liquid facets is the substrate of Fat facets." Genes Dev 16(3): 289-94.

Chung, C. H. and S. H. Baek (1999). "Deubiquitinating enzymes: their diversity and emerging roles." Biochem Biophys Res Commun 266(3): 633-40.

Chung, K. K., V. L. Dawson, et al. (2003). "New insights into Parkinson's disease." J Neurol 250 Suppl 3: 11115-24.

Ciardiello, F. and G. Tortora (2001). "A novel approach in the treatment of cancer: targeting the epidermal growth factor receptor." Clin Cancer Res 7(10): 2958-70.

Ciechanover, A. (2001). "Ubiquitin-mediated degradation of cellular proteins: why destruction is essential for construction, and how it got from the test tube to the patient's bed." Isr Med Assoc J 3(5): 319-27.

Ciechanover, A. (2003). "The ubiquitin proteolytic system and pathogenesis of human diseases: a novel platform for mechanism-based drug targeting." Biochem Soc Trans 31(2): 474-81.

Conaway, R. C., C. S. Brower, et al. (2002). "Emerging roles of ubiquitin intranscription regulation." Science 296(5571): 1254-8.

Clague and Urbe (2001). "The interface of receptor trafficking and signalling." J Cell Sci 114(Pt 17): 3075-81.

Cupillard, L., et al. (1997) Cloning, Chromosomal Mapping, and Expression of a Novel Human Secretory Phospholipase A2. J. Biol. Chem. 272(25): p. 15745-15752.

Curcio-Morelli, C., A. M. Zavacki, et al. (2003). "Deubiquitination of type 2 iodothyronine deiodinase by von Hippel-Lindau prot-interacting deubiquit enzymes reg thyroid hormone activation." J Clin Invest 112(2): 189-96.

D'Andrea and Pellman (1998) "Deubiquit enz: new class of biol reg" Crit Rev Biochem Mol Biol 33(5): 337-52.

Dang, L. C., F. D. Melandri, et al. (1998). "Kinetic and mechanistic studies on the hydrolysis of ubiquitin C-terminal 7-amido-4-methylcoumarin by deubiquitinating enzymes." Biochemistry 37(7): 1868-79.

Day, I. N., L. J. Hinks, et al. (1990). "The structure of the human gene encoding protein gene product 9.5 (PGP9.5), a neuron-specific ubiquitin C-terminal hydrolase." Biochem J 268(2): 5214.

Dennis (1994) Div group types, reg and funct of phospholipase A2 J Biol Chem 269(18): 13057-13060.

Dijkstra, Drenth & Kalk, (1981) Active site and catal mech of phospholipase A2. Nature. 289(5798): 604-6.

Dijkstra et al. (1984). "Role of the N-terminus in the interaction of pancreatic phospholipase A2 with aggregated substrates. Properties and crystal structure of transaminated phospholipase A2." Biochemistry 23(12): 2759-66.

Dubiel and Gordon (1999). "Ubiquitin pathway: link in the polyubiquitin chain?" Curr Biol 9(15): R554-7.

Everett, R. D., M. Meredith, et al. (1997). "A novel ubiquitin-specific protease is dynamically associated with the PML nuclear domain and binds to a herpesvirus regulatory protein." Embo J 16(3): 566-77.

Frederick et al. (1998) "The human UNP locus at 3p21.31 enc 2 tissue-select, cytopl isoforms with deubiquit activity that have reduced expression in small cell lung carcinoma cell lines." Oncogene 16(2): 153-65.

Gan-Erdene et al (2003) Ident & charact of DEN1, a denedylase of ULP fam J Biol Chem 278(31):28892-900

Gelb, M. H., et al., (1995) Interfacial Enzymology of Glycerolipid Hydrolases: Lessons from Secreted Phospholipases A2. Annual Review of Biochemistry 64(1): p. 653-688.

Glickman & Ciechanover (2002) The ubiquitin-proteasome proteolytic pathway: destruction for the sake of construction Physiol Rev. April; 82(2):373-428.

Gnarra et al. (1994). "Mutations of the VHL tumour suppressor gene in renal carcinoma." Nat Genet 7(1): 85-90.

Gohara, D. W., C. S. Ha, et al. (1999). "Production of "authentic" poliovirus RNA-dependent RNA polymerase (3 D(pol)) by ubiquitin-protease-mediated cleavage in Escherichia coli." Protein Expr Purif 17(1): 128-38.

Gong, L., T. Kamitani, et al. (2000). "Identification of a novel isopeptidase with dual specificity for ubiquitin- and NEDD8-conjugated proteins." J Biol Chem 275(19): 14212-6.

Gong et al. (2000) "Diff reg of sentrinized prot by novel sentrin-specific protease." J Biol Chem 275(5): 3355-9.

Graner et al (2004) "Isopeptidase USP2a reg stab of fatty ac synthase in prost cancer" Cancer Cell 5(3):253-61.

Grataroli, R., et al., Studies on prophospholipase A2 and its enzyme from human pancreatic juice. Catalytic properties and sequence of the N-terminal region. Eur J Biochem, 1982. 122(1): p. 111-7.

Gray, D. A., J. Inazawa, et al. (1995). "Elevated expression of Unph, a proto-oncogene at 3p21.3, in human lung tumors." Oncogene 10(11): 2179-83.

Gupta, K., et al. (1994). "The Unp proto-oncogene encodes a nuclear protein." Oncogene 9(6): 1729-31.

Hadari, T., J. V. Warms, et al. (1992). "A ubiquitin C-terminal isopeptidase that acts on polyubiquitin chains. Role in protein degradation." J Biol Chem 267(2): 719-27.

Hansen et al. (1997). "Structure of the RNA-dependent RNA polymerase of poliovirus." Structure 5(8): 1109-22.

Hemelaar, J., A. Borodovsky, et al. (2004). "Specific and covalent targeting of conjugating and deconjugating enzymes of ubiquitin-like proteins." Mol Cell Biol 24(1): 84-95.

Hendstrand, J. M., Schmid, J., and Amrheim, N (1995). "Only the Mature Form of the Platidic Chorismate Synthase Is Enzymatically Active." Plant Physiol 108: 1127-1132.

Henriksen, R. A., C. K. Dunham, et al. (1998). "Prothrombin Greenville, Arg517-->Gln, identified in an individual heterozygous for dysprothrombinemia." Blood 91(6): 2026-31.

Hershko, A. and A. Ciechanover (1998). "The ubiquitin system." Annu Rev Biochem 67: 425-79.

Hicke, L. (2001). "Protein regulation by monoubiquitin." Nat Rev Mol Cell Biol 2(3): 195-201.

Hochstrasser, M. (1996). "Ubiquitin-dependent protein degradation." Annu Rev Genet 30: 405-39.

Hochstrasser, M. (2002). "Molecular biology. New proteases in a ubiquitin stew." Science 298(5593): 549-52.

Hofmann & Pickart (2001) "In vitro assemb/recogn of Lys-63 polyubiq chains" J Biol Chem 276(30):27936-43.

Hong, T. M., P. C. Yang, et al. (2000). "Profiling the downstream genes of tumor suppressor PTEN in lung cancer cells by complementary DNA microarray." Am J Respir Cell Mol Biol 23(3): 355-63.

Huang, Y., R. T. Baker, et al. (1995). "Control of cell fate by a deubiquitinating enzyme encoded by the fat facets gene." Science 270(5243): 1828-31.

Jensen, D. E., M. Proctor, et al. (1998). "BAP1: a novel ubiquitin hydrolase which binds to the BRCA1 RING finger and enhances BRCA1-mediated cell growth suppression." Oncogene 16(9): 1097-112.

Johnson, E. S., P. C. Ma, et al. (1995). "A proteolytic pathway that recognizes ubiquitin as a degradation signal." J Biol Chem 270(29): 17442-56.

Johnston, S. C., C. N. Larsen, et al. (1997). "Crystal structure of a deubiquitinating enzyme (human UCH-L3) at 1.8 A resolution." Embo J 16(13): 3787-96.

Kato, G. J. (1999). "Human genetic diseases of proteolysis." Hum Mutat 13(2): 87-98.

Kawakami, T., T. Suzuki, et al. (1999). "Isolation and characterization of cytosolic and membrane-bound deubiquitinylating enzymes from bovine brain." J Biochem (Tokyo) 126(3): 612-23.

Kitada et al (1998) "Mutat in parkin gene cause autos recess juvenile parkinsonism" Nature 392(6676): 605-8.

Kostin et al (2003). "Myocytes die by multiple mechanisms in failing human hearts." Circ Res 92(7): 715-24.

Larsen, C. N., J. S. Price, et al. (1996). "Substrate binding and catalysis by ubiquitin C-terminal hydrolases: identification of two active site residues." Biochemistry 35(21): 6735-44.

LaVallie, E. R., A. Rehemtulla, et al. (1993). "Cloning and functional expression of a cDNA encoding the catalytic subunit of bovine enterokinase." J Biol Chem 268(31): 23311-7.

Layfield, R., K. Fraklin, et al. (1999). "Chemically synthesized ubiquitin extension proteins detect distinct catalytic capacities of deubiquitinating enzymes." Anal Biochem 274(1): 40-9.

Le Roy (2005) "Clathrin- and non-clathrin-med endocyt reg of cell signalling" Nat Rev Mol Cell Biol 6(2):112-26

Lee (1998) "Proteasome inhibitors: valuable new tools for cell biologists." Trends Cell Biol 8(10): 397-403.

Leroy, E., R. Boyer, et al. (1998). "The ubiquitin pathway in Parkinson's disease." Nature 395(6701): 451-2.

Li et al (2002) "Deubiquit of p53 by HAUSP is pathway for p53 stabil" Nature 416(6881): 648-53.

Li & Hochstrasser (1999) "New protease req for cell-cycle progression in yeast." Nature 398(6724): 246-51.

Li, S. J. and M. Hochstrasser (2000). "The yeast ULP2 (SMT4) gene encodes a novel protease specific for the ubiquitin-like Smt3 protein." Mol Cell Biol 20(7): 2367-77.

Li, Z., X. Na, et al. (2002). "Ubiquitination of a novel deubiquitinating enzyme requires direct binding to von Hippel-Lindau tumor suppressor protein." J Biol Chem 277(7): 4656-62.

Lin, H., A. Keriel, et al. (2000). "Divergent. N-terminal sequences target an inducible testis deubiquitinating enzyme to distinct subcellular structures." Mol Cell Biol 20(17): 6568-78.

Lin, H., L. Yin, et al. (2001). "Divergent N-terminal sequences of a deubiquitinating enzyme modulate substrate specificity." J Biol Chem 276(23): 20357-63.

Lisztwan, J., G. Imbert, et al. (1999). "The von Hippel-Lindau tumor suppressor protein is a component of an E3 ubiquitin-protein ligase activity." Genes Dev 13(14): 1822-33.

Lockhart (2005) "Epid growth factor rec as target for colorectal cancer therapy" Semin Oncol 32(1): 52-60.

LoRusso, P. M., R. S. Herbst, et al. (2003). "Improvements in quality of life and disease-related symptoms in phase I trials of the selective oral epidermal growth factor receptor tyrosine kinase inhibitor ZD1839 in non-small cell lung cancer and other solid tumors." Clin Cancer Res 9(6): 2040-8.

Lu, S., R. Halberg, et al. (1990). "Processing of the mother-cell sigma factor, sigma K, may depend on events occurring in the forespore during *Bacillus subtilis* development." Proc Natl Acad Sci USA 87(24): 9722-6.

Lundgren, J., P. Masson, et al. (2003). "Use of RNA interference and complementation to study the function of the *Drosophila* and human 26S proteasome subunit S13." Mol Cell Biol 23(15): 5320-30.

Maher, E. R. and W. G. Kaelin, Jr. (1997). "von Hippel-Lindau disease." Medicine (Baltimore) 76(6): 381-91.

Malakhov, M. P., Kim, K. I., Malakhova, O. A., Jacobs, B. S., Borden, E. C., Zhang, D.-E. (2003). High-throughput Immunoblotting. Ubiquitine-like Protein ISG15 Modifies Key Regulators of Signal Transduction, J. Biol. Chem. 278: 16608-16613

Malakhova et al (2002) Lipopolys Act Expr of ISG15-specific Protease UBP43 via Interferon Regulatory Factor 3. J. Biol. Chem. 277: 14703-14711

Malakhov et al (2002) UBP43 (USP18) Spec Removes ISG15 from Conj Prot J. Biol. Chem. 277: 9976-9981

Maraganore et al. (2004). "UCHL1 is a Parkinson's disease susceptibility gene." Ann Neurol 55(4): 512-21.

Mei & Zalkin (1990) Amino-term del define glutamine amide transfer domain in glutamine phosphoribosylpyrophosphate amidotransferase & PurF-type amidotransferases. J. Bacteriol. 172: 3512-3514

Malakhov et al (2004). "SUMO fusion and SUMO-specific proteases for efficient expression and purification of proteins." J. Structural and Functional Genomics (in press).

Mantsala & Zalkin (1976) "Glutamate synth Prop of glutamine-dependentact" J Biol Chem 251(11): 3294-9.

Matsuka et al. (1999). "Fibrinogen cleavage by the *Streptococcus pyogenes* extracellular cysteine protease and generation of antibodies that inhibit enzyme proteolytic activity." Infect Immun 67(9): 4326-33.

McCullough et al. (2004). "AMSH is an endosome-assoc ubiquitin isopeptidase." J Cell Biol 166(4): 487-92.

Messenger, L. J., and H. Zalkin (1979) "Glutamine phosphoribosylpyrophosphate amidotransferase from *Escherichia coli*. Purification and properties." J Biol Chem 254(9): 3382-92

Mimnaugh, E. G., G. Kayastha, et al. (2001). "Caspase-dependent deubiquitination of monoubiquitinated nucleosomal histone H2A induced by diverse apoptogenic stimuli." Cell Death Differ 8(12): 1182-96.

Mossessova, E. and C. D. Lima (2000). "Ulp1-SUMO crystal structure and genetic analysis reveal conserved interactions and a regulatory element essential for cell growth in yeast." Mol Cell 5(5): 865-76.

Muchmore, C. R., J. M. Krahn, et al. (1998). "Crystal structure of glutamine phosphoribosylpyrophosphate amidotransferase from *Escherichia coli*." Protein Sci 7(1): 39-51.

Ohh, M., C. W. Park, et al. (2000). "Ubiquitination of hypoxia-inducible factor requires direct binding to the beta-domain of the von Hippel-Lindau protein." Nat Cell Biol 2(7): 423-7.

Oliver, G., Gosset G, Sanchez-Pescadore, E. et al (1987) Determination of the sequence for the gluiamate synthetase structural gene of *E. coli* K-12. Gene 60: 1-11

O'Reilly et al (1992). Chapters 11, 12. Baculovirus expression vectors: a laboratory manual. NY, Freeman.

Padmanabhan et al (1993) "Struct of human des(1-45) factor Xa at 2.2 A resolution." J Mol Biol 232(3): 947-66.

Papa et al (1999) "Inter of Doa4 deubiquitinating enz with yeast 26S proteasome." Mol Biol Cell 10(3): 741-56.

Papa, F. R. and M. Hochstrasser (1993). "The yeast DOA4 gene encodes a deubiquitinating enzyme related to a product of the human tre-2 oncogene." Nature 366(6453): 313-9.

Park, E. C., D. Finley, and J. W. Szostak (1992) A strategy for the generation of conditional mutations by protein destabilization. Proc. Natl. Acad. Sci. USA 89:1249-1252.

Park et al (2000) "Tissue-specif, funct charact & subcellular local of rat ubiquitin-specific process protease, UBP109, whose mRNA expression is developmentally regulated." Biochem J 349(Pt 2): 443-53.

Piccinini, M., A. Merighi, et al. (1996). "Affinity purification and characterization of protein gene product 9.5 (PGP9.5) from retina." Biochem J 318 (Pt 2): 711-6.

Pickart, C. M. (2001). "Mechanisms underlying ubiquitination." Annu Rev Biochem 70: 503-33.

Puddicombe, S. M., R. Polosa, et al. (2000). "Involvement of the epidermal growth factor receptor in epithelial repair in asthma." Faseb J 14(10): 1362-74.

Rossi, S., E. Graner, et al. (2003). "Fatty acid synthase expression defines distinct molecular signatures in prostate cancer." Mol Cancer Res 1(10): 707-15.

Sims, K. B. (2001). "Von Hippel-Lindau disease: gene to bedside." Curr Opin Neurol 14(6): 695-703.

Sambook, J., E. Fritsch, and T. Maniatis (1989) Molecular Cloning: A Laboratory Manual, Second Edition. Cold Spring Harbor Laboratory, Cold Spring Harbor, N.Y.

Sakai, K., S. Ren, et al. (1996). "A novel heparin-dependent processing pathway for human tryptase. Autocatalysis followed by activation with dipeptidyl peptidase I." J Clin Invest 97(4): 988-95.

Schechter, N. M., J. L. Sprows, et al. (1989). "Reaction of human skin chymotrypsin-like proteinase chymase with plasma proteinase inhibitors." J Biol Chem 264(35): 21308-15.

Shah et al. (2002). "Ubiquitin proteasome inhibition and cancer therapy." Surgery 131(6): 595-600.

Sizmann, D., C. Keilmann, et al. (1990). "Primary structure requirements for the maturation in vivo of penicillin acylase from *Escherichia coli* ATCC 11105." Eur J Biochem 192(1): 143-51.

Smyth, M. J., M. D. O'Connor, et al. (1996). "Granymes: a variety of serine protease specificities encoded by genetically distinct subfamilies." J Leukoc Biol 60(5): 555-62.

Sommerhoff (1989) "Mast cell chymase, secretagogue for airway gland serous cells" J Immunol 142(7):2450-6.

Spano, J. P., R. Fagard, et al. (2005). "Epidermal growth factor receptor signaling in colorectal cancer: preclinical data and therapeutic perspectives." Ann Oncol 16(2): 189-94.

Stefanis, L., K. E. Larsen, et al. (2001). "Expression of A53T mutant but not wild-type alpha-synuclein in PC12 cells induces alterations of the ubiquitin-dependent degradation system, loss of dopamine release, and autophagic cell death." J Neurosci 21(24): 9549-60.

Steffan et al (2004) "SUMO mod of Huntingtin & Huntington's disease pathology." Science 304 (5667): 100-4.

Stein et al (1995) "Kinetic st of isopeptidase T: modul of peptidase act by ubiquitin" Biochem 34(39): 12616-23.

Stolle, C., G. Glenn, et al. (1998). "Improved detection of germline mutations in the von Hippel-Lindau disease tumor suppressor gene." Hum Mutat 12(6): 417-23.

Stroud et al. (1977). "Mechanisms of zymogen activation." Annu Rev Biophys Bioeng 6: 177-93.

Swinney, D. C. (2001). "Targeting protein ubiquitination for drug discovery. What is in the drug discovery toolbox?" Drug Discov Today 6(5): 244-250.

Takatsuji, H., H. Yamauchi, et al. (1992). "Cauliflower mosaic virus reverse transcriptase. Activation by proteolytic processing and functional alteration by terminal deletion." J Biol Chem 267(16): 11579-85.

Takeyama, K., J. V. Fahy, et al. (2001). "Relationship of epidermal growth factor receptors to goblet cell production in human bronchi." Am J Respir Crit Care Med 163(2): 511-6.

Tobias, J. W. and A. Varshavsky (1991). "Cloning and functional analysis of the ubiquitin-specific protease gene UBP1 of *Saccharomyces cerevisiae*." J Biol Chem 266 (18): 12021-8.

Toda et al (2003) "Identif of susceptibility genes for sporadic Parkinson's disease." J Neurol 250 Suppl 3:11140-3.

Tung, C. H., et al., (1999) Preparation of a cathepsin D sensitive near-infrared fluorescence probe for imaging. Bioconjug Chem 10(5): p. 892-6.

Tyers, M. and R. Rottapel (1999). "VHL: a very hip ligase." Proc Natl Acad Sci USA 96(22): 12230-2.

Tso, J. Y., M. A. Hermodson, et al. (1982). "Glutamine phosphoribosylpyrophosphate amidotransferase from cloned *Escherichia coli* purF. NH2-terminal amino acid sequence, identification of the glutamine site, and trace metal analysis." J Biol Chem 257(7): 3532-6.

Varshavsky A. (1996) The N-end rule: functions, mysteries, uses. Proc. Natl. Acad. Sci USA 93:12142-12149.

Venkateswarlu, D., L. Perera, et al. (2002). "Structure and dynamics of zymogen human blood coagulation factor X." Biophys J 82(3): 1190-206.

Verma, R., L. Aravind, et al. (2002). "Role of Rpn11 metalloprotease in deubiquitination and degradation by the 26S proteasome." Science 298(5593): 611-5.

von Ahsen & Bomer (2005). "High-Throughput Screening for Kinase Inhibitors." Chembiochem 6(3): 481-490.

Vu & Sakamoto (2000) "Ubiquitin-mediated proteolysis and human disease." Mol Genet Metab 71(1-2): 261-6.

Walls (1998) Mast cell proteases in asthma. Inflamm mech in asthma Holgate, Busse, W W. NY, Marcel Dekker.

Wang, Q. M., R. B. Johnson, et al. (1998). "Enzymatic characterization of refolded human rhinovirus type 14 2A protease expressed in *Escherichia coli*." J Virol 72(2): 1683-7.

Wang, Q. M., R. B. Johnson, et al. (1997). "A continuous colorimetric assay for rhinovirus-14 3C protease using peptide p-nitroanilides as substrates." Anal Biochem 252 (2): 238-45.

Wang, Q. M., R. B. Johnson, et al. (1998). "Dual inhibition of human rhinovirus 2A and 3C proteases by homophthalimides." Antimicrob Agents Chemother 42(4): 916-20.

Wang Z., M. Walter, T, Selwood, H. Rubin and N. M. Schechter (1998) "Recombinant Expression of human mast cell proteases chymase and tryptase." Biol Chem 379(2): 167-74.

Weissleder, R., et al., (1999) In vivo imaging of tumors with protease-activated near-infrared fluorescent probes. Nat Biotechnol, 17(4): p. 375-8.

Weissman, A. M. (2001). "Themes and variations on ubiquitylation." Nat Rev Mol Cell Biol 2(3): 169-78.

Wilkinson (1997). "Reg of ubiquitin-dep processes by deubiquitinating enzymes." Faseb J 11 (14): 1245-56.

Wilkinson, K. D. (2000). "Ubiquitination and deubiquitination: targeting of proteins for degradation by the proteasome." Semin Cell Dev Biol 11(3): 141-8.

Wilkinson, K. D., M. J. Cox, et al. (1986). "Synthesis and characterization of ubiquitin ethyl ester, a new substrate for ubiquitin carboxyl-terminal hydrolase." Biochemistry 25(21): 6644-9.

Wilkinson, K. D. a. H., M. (1998). Ubiquitin and the biology of the cell. H. J. R. Peters J. M., Finley D. New York, Plenum Press: 99-125.

Wong, S., T. H. Morales, et al. (1990). "Ubiquitin-EP52 fusion protein homologs from *Trypanosoma brucei*." Nucleic Acids Res 18(23): 7181.

Woo (1995) "Multiple ubiquitin C-term hydrolases from chick skeletal muscle" J Biol Chem 270(32):18766-73.

Wood (2002 "Dubble or nothing? Is HAUSP deubiquit enz arbiter of p53 levels?" Sci STKE 2002(143): PE34.

Yamagishi, H., V. Garg, et al. (1999). "A molecular pathway revealing a genetic basis for human cardiac and craniofacial defects." Science 283(5405): 1158-61.

Yan, N., J. H. Doelling, et al. (2000). "The ubiquitin-specific protease family from *Arabidopsis*. AtUBP1 and 2 are required for the resistance to the amino acid analog canavanine." Plant Physiol 124(4): 1828-43.

Yao, T. and R. E. Cohen (2002). "A cryptic protease couples deubiquitination and degradation by the proteasome." Nature 419(6905): 403-7.

Yuan, C., et al. (1999) Structural analysis of phospholipase A2 from functional perspective. 1. Functionally relevant solution structure and roles of the hydrogen-bonding network. Biochemistry. 38(10): p. 2909-18.

Zalkin, H. (1993). "The amidotransferases." Adv Enzymol Relat Areas Mol Biol 66: 203-309.

Zhu, Y., M. Carroll, et al. (1996). "DUB-1, a deubiquitinating enzyme with growth-suppressing activity." Proc Natl Acad Sci USA 93(8): 3275-9.

Zhu, Y., K. Lambert, et al. (1997). "DUB-2 is a member of a novel family of cytokine-inducible deubiquitinating enzymes." J Biol Chem 272(1): 51-7.

---

We claim:

1. A method for assessing the activity of a proteolytic enzyme, said method comprising:
   (a) providing a fusion polypeptide comprising:
      (i) a first polypeptide that comprises Ubiquitin or a Ubiquitin-like protein (UBL), and
      (ii) a second polypeptide comprising an amino acid sequence having a free N-terminal amino acid required for enzymatic activation and detection, wherein said second polypeptide is an enzyme;
   wherein the first and second polypeptides are operatively linked to one another through the first polypeptide C-terminus and the second polypeptide N-terminus, and wherein said second polypeptide is enzymatically inactive when operatively linked to said first polypeptide in said fusion polypeptide;
   (b) contacting the fusion polypeptide with the proteolytic enzyme to produce a cleaved first polypeptide and a cleaved second polypeptide, wherein said cleaved second polypeptide has enzymatic activity;
   (c) detecting a signal associated with the enzymatic activity of the cleaved second polypeptide; and
   (d) establishing a correlation between the signal associated with the enzymatic activity of the cleaved second polypeptide and the activity of the proteolytic enzyme, thereby determining the activity of the proteolytic enzyme,
   wherein the second polypeptide is selected from the group consisting of a 3Dpol RNA-dependent RNA polymerase, GPATase, tryptase, enterokinase, and phospholipase.

2. The method of claim 1, further comprising normalizing each enzyme or sample cleavage signal by reference to 0% and 100% cleavage signals and assigning a proteolytic enzyme activity value to each enzyme or sample thereof; wherein when the enzyme activity obtained is below a cut-off value it may be said that the enzyme or sample is inactive and when it above the cut-off value it is active.

3. The method of claim 2, wherein the 0% and 100% cleavage signals are obtained by repeating the contacting, detecting and establishing steps for full cleavage and full inhibition of proteolytic enzyme activity to obtain the 100% and 0% cleavage signals.

4. The method of claim 2, wherein the normalizing step is conducted by normalizing each enzyme or sample cleavage signal by reference to a curve of enzyme activity cleavage values and assigning a proteolytic enzyme activity to each enzyme or sample thereof; wherein when the enzyme activity obtained is below a cut-off value it may be said that the enzyme or sample is inactive and when it above the cut-off value it is active.

5. The method of claim 1, wherein said UBL is selected from the group consisting of SUMO, Nedd8, ISG15, Apg8, Apg12, FAT10, Urm1, Hub, UBi, Rub1, and ISG15.

6. The method of claim 1, wherein said signal associated with the enzymatic activity of the cleaved second polypeptide comprises a radioactive, fluorescent, phosphorescent, chromogenic, sonogenic, or chemiluminescent signal.

7. The method of claim 1, wherein the first and second polypeptides are covalently linked to one another.

8. The method of claim 1, wherein the first and second polypeptides are operatively linked through a linker.

9. The method of claim 8, wherein the linker comprises at least one amino acid.

10. The method of claim 1, wherein the fusion polypeptide comprises a fusion protein.

11. The method of claim 1, wherein the proteolytic enzyme comprises an isopeptidase.

12. The method of claim 1, wherein the proteolytic enzyme comprises a ubiquitin C-terminal hydrolase, ubiquitin-specific protease.

13. The method of claim 1, wherein the proteolytic enzyme comprises a protein selected from the group consisting of ULP1, ULP2, SENP1, SENP2, yeast YUH1, mammalian UCHL1, UCH-L3, UCH37, Bap1, USP-M, USP7, UNP, CYLD, CYLD1, KIAA0849, USP9X, DFFRX, USP9, FAFX, USP9Y, DFFRY, USP10, FAFY, OTUB1, OTB1, OUT1, HSPC263, OTUB2, C14orf137, OTB2, OUT2, KIAA0190, USP11, UHX1, USP12, UBH1m, USP12L1, USP13, ISOT3, USP14, TGT, USP15, KIAA0529, USP16, UBPM, USP18, UBP43, USP19, KIAA0891, ZMYND9, USP20, KIAA1003, LSFR3A, USP21, USP23, NEDD8-specific protease, USP22, KIAA1063, USP24, KIAA1057, USP25, USP26, USP28, USP29, USP30, USP32, USP33, KIAA1097, VDU1, USP35, KIAA1372, USP34, USP36, KIAA1453, USP37, KIAA1594, USP38, KIAA1891, USP40, USP42, USP44, USP46, USP49, USP51, UBP1, USP1, UBP2, USP2, UBP41, UBP3, USP3, UBP4, USP4, UNPH, UBP5, USPS, ISOT, UBP6, USP6, TRE2, UBP7, USP7, HAUSP, UBP8, USP8, KIAA0055, UBPY, VCIP, VCIP135, KIAA1850, Cezanne1, Cezanne2, A20, UCH-L1, Park5, UCH-L5, UCH-37, ATXN3, ATX3, MJD, MJD1, SCA3, POH1, PSMD14, CSN5, COPS5, JAB1, SENP3, SSP3, SUSP3, SENP5, FKSG45, SENP6, FKSG6, KIAA0797, SSP1, SUSP1, SENP7, KIAA1707, SSP2, SUSP2, SENP8, FKSG8, PRSC2, DUB1, DUB2, DUB3, and DUB4.

14. The method of claim 1, further comprising expressing a polynucleotide encoding the fusion protein under conditions effective for expression thereof.

15. The method of claim 14, wherein the polynucleotide is expressed in a eukaryotic cell, or fraction or extract thereof.

16. The method of claim 14, further comprising isolating the fusion protein and, optionally, purifying the fusion protein.

17. The method of claim 1, further comprising
repeating the contacting, detecting and establishing steps in the presence of a sample suspected of comprising a proteolytic enzyme activity modulator; and
determining a value for the effect of the sample on the proteolytic enzyme activity by reference between the sample signal and the corresponding enzyme activity signal obtained in the absence of sample.

18. The method of claim 16, wherein the sample comprises a physiological fluid, a tissue sample, a cell, or a cell fraction.

19. The method of claim 1, wherein at least one step is conducted in vitro, in a cell, in a cell extract, or in a tissue extract.

20. The method of claim 17, wherein the contacting, detecting, establishing and determining steps are conducted separately for a plurality of samples suspected of comprising a proteolytic enzyme activity modulator to obtain a value for the effect of the sample on the proteolytic enzyme activity.

21. The method of claim 20, which is automated.

22. The method of claim 20, which collects, processes and reports on information obtained for each sample and controls.

23. The method of claim 1, wherein the step of detecting further comprises determining the amount of activity of the cleaved second polypeptide.

24. The method of claim 1, wherein the second polypeptide comprises a protein selected from the group consisting of a 3Dpol RNA-dependent RNA polymerase, GPATase, tryptase, and phospholipase A2.

25. The method of claim 24, wherein the second polypeptide comprises phospholipase A2.

* * * * *